US009797899B2

(12) United States Patent
Bornheimer et al.

(10) Patent No.: US 9,797,899 B2
(45) Date of Patent: Oct. 24, 2017

(54) MICROFLUIDIC DEVICES, AND METHODS OF MAKING AND USING THE SAME

(71) Applicant: Becton, Dickinson and Company, Franklin Lakes, NJ (US)

(72) Inventors: Scott Joseph Bornheimer, Berkeley, CA (US); Jeffrey Sugarman, Los Altos, CA (US); Wei Huang, Cupertino, CA (US); Edward Michael Goldberg, Los Gatos, CA (US); Ming Tan, Danville, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 276 days.

(21) Appl. No.: 14/533,949

(22) Filed: Nov. 5, 2014

(65) Prior Publication Data

US 2015/0125882 A1 May 7, 2015

Related U.S. Application Data

(60) Provisional application No. 61/900,590, filed on Nov. 6, 2013.

(51) Int. Cl.

*G01N 33/558* (2006.01)
*B01F 13/00* (2006.01)
(Continued)

(52) U.S. Cl.

CPC ......... *G01N 33/558* (2013.01); *B01F 5/0691* (2013.01); *B01F 13/0059* (2013.01);
(Continued)

(58) Field of Classification Search

CPC ................ B01F 5/0691; B01F 13/0059; B01F 3/502746; B01F 13/0061;
(Continued)

(56) References Cited

U.S. PATENT DOCUMENTS 3,819,913 A 6/1974 Carter et al.
3,916,205 A 10/1975 Kleinerman
(Continued)

FOREIGN PATENT DOCUMENTS

DE 102009016712 A1 10/2010
EP 0737855 A1 10/1996
(Continued)

OTHER PUBLICATIONS

Yager et al. Microfluidic diagnostic technologies for global public health. Nature 442 (27): 412-418 (Jul. 2006).*
(Continued)

*Primary Examiner* — Gail R Gabel
(74) *Attorney, Agent, or Firm* — Khin K. Chin; Bret E. Field; Bozicevic, Field & Francis LLP

(57) ABSTRACT

The present disclosure provides methods and systems for assaying a sample. A microfluidic device to perform an assay of a sample (e.g., biological sample) is described having a sample application site, a porous component and a flow channel. The porous component provides for uniform dissolution of a reagent and mixing of the sample and reagent without filtering the sample.

19 Claims, 3 Drawing Sheets

(51) Int. Cl.
*B01F 5/06* (2006.01)
*B01L 3/00* (2006.01)

(52) U.S. Cl.
CPC .... *B01F 13/0061* (2013.01); *B01L 3/502746* (2013.01); *B01F 2215/0431* (2013.01); *B01L 3/5023* (2013.01); *B01L 2200/16* (2013.01); *B01L 2300/0816* (2013.01); *B01L 2400/0406* (2013.01); *B01L 2400/086* (2013.01)

(58) Field of Classification Search
CPC ........... B01F 2215/0431; G01N 33/558; B01L 3/502746; B01L 2400/086; B01L 2400/0406; B01L 2200/16; B01L 2300/0816; B01L 3/5023
See application file for complete search history.

(56) References Cited

U.S. PATENT DOCUMENTS

| | | | |
|---|---|---|---|
| 3,963,350 | A | 6/1976 | Watanabe et al. |
| 4,088,448 | A | 5/1978 | Lilja et al. |
| 4,125,828 | A | 11/1978 | Resnick et al. |
| 4,133,873 | A | 1/1979 | Noller |
| 4,337,222 | A | 6/1982 | Kitajima et al. |
| 4,501,496 | A | 2/1985 | Griffin |
| 4,586,190 | A | 4/1986 | Tsuji |
| 4,727,020 | A | 2/1988 | Recktenwald |
| 4,751,188 | A | 6/1988 | Valet |
| 4,857,735 | A | 8/1989 | Noller |
| 4,959,305 | A | 9/1990 | Woodrum |
| 5,053,626 | A | 10/1991 | Tillotson |
| 5,073,857 | A | 12/1991 | Peters et al. |
| 5,102,625 | A | 4/1992 | Milo |
| 5,134,662 | A | 7/1992 | Bacus et al. |
| 5,159,642 | A | 10/1992 | Kosaka |
| 5,187,749 | A | 2/1993 | Sugimoto |
| 5,196,709 | A | 3/1993 | Berndt |
| 5,200,152 | A | 4/1993 | Brown |
| 5,294,799 | A | 3/1994 | Aslund et al. |
| 5,332,905 | A | 7/1994 | Brooker et al. |
| 5,348,859 | A | 9/1994 | Brunhouse et al. |
| 5,385,539 | A | 1/1995 | Maynard |
| 5,489,771 | A | 2/1996 | Beach et al. |
| 5,491,343 | A | 2/1996 | Brooker |
| 5,528,045 | A | 6/1996 | Hoffman et al. |
| 5,547,849 | A | 8/1996 | Baer et al. |
| 5,554,536 | A | 9/1996 | Rising |
| 5,556,764 | A | 9/1996 | Sizto et al. |
| 5,592,291 | A | 1/1997 | Iida |
| 5,599,668 | A | 2/1997 | Stimpson et al. |
| 5,627,037 | A | 5/1997 | Ward et al. |
| 5,661,558 | A | 8/1997 | Nogami et al. |
| 5,674,457 | A | 10/1997 | Williamsson et al. |
| 5,675,155 | A | 10/1997 | Pentoney et al. |
| 5,681,529 | A | 10/1997 | Taguchi et al. |
| 5,692,503 | A | 12/1997 | Kuenstner |
| 5,732,150 | A | 3/1998 | Zhou et al. |
| 5,733,721 | A | 3/1998 | Hemstreet et al. |
| 5,773,301 | A | 6/1998 | Ziegler |
| 5,851,835 | A | 12/1998 | Groner |
| 5,898,487 | A | 4/1999 | Hage |
| 6,043,880 | A | 3/2000 | Andrews et al. |
| 6,064,474 | A | 5/2000 | Lee et al. |
| 6,064,897 | A | 5/2000 | Lindberg et al. |
| 6,094,592 | A | 7/2000 | Yorkey et al. |
| 6,103,197 | A | 8/2000 | Werner |
| 6,154,282 | A | 11/2000 | Lilge et al. |
| 6,159,740 | A | 12/2000 | Hudson et al. |
| 6,181,418 | B1 | 1/2001 | Palumbo et al. |
| 6,187,592 | B1 | 2/2001 | Gourley |
| 6,214,629 | B1 | 4/2001 | Freitag et al. |
| 6,226,347 | B1 | 5/2001 | Golenhoffen |
| 6,262,798 | B1 | 7/2001 | Shepherd et al. |
| 6,294,094 | B1 | 9/2001 | Muller et al. |
| 6,305,804 | B1 | 10/2001 | Rice et al. |
| 6,342,376 | B1 | 1/2002 | Kozian et al. |
| 6,345,191 | B1 | 2/2002 | Hartmann et al. |
| 6,350,613 | B1 | 2/2002 | Wardlaw et al. |
| 6,410,341 | B1 | 6/2002 | Freitag et al. |
| 6,453,060 | B1 | 9/2002 | Riley et al. |
| 6,477,394 | B2 | 11/2002 | Rice et al. |
| 6,479,299 | B1 | 11/2002 | Parce et al. |
| 6,493,567 | B1 | 12/2002 | Krivitski et al. |
| 6,519,025 | B2 | 2/2003 | Shepherd et al. |
| 6,563,585 | B1 | 5/2003 | Rao et al. |
| 6,594,075 | B1 | 7/2003 | Kanao |
| 6,611,320 | B1 | 8/2003 | Lindberg et al. |
| 6,612,111 | B1 | 9/2003 | Hodges |
| 6,638,769 | B2 | 10/2003 | Lilja et al. |
| 6,665,060 | B1 | 12/2003 | Zahniser et al. |
| 6,696,240 | B1 | 2/2004 | Kloepfer et al. |
| 6,716,588 | B2 | 4/2004 | Sammak et al. |
| 6,723,290 | B1 | 4/2004 | Wardlaw |
| 6,740,527 | B1 | 5/2004 | Wong et al. |
| 6,825,921 | B1 | 11/2004 | Modlin et al. |
| 6,828,567 | B2 | 12/2004 | Amirkhanian et al. |
| 6,831,733 | B2 | 12/2004 | Pettersson et al. |
| 6,858,400 | B2 | 2/2005 | Bristow |
| 6,862,534 | B2 | 3/2005 | Sterling et al. |
| 6,869,570 | B2 | 3/2005 | Wardlaw |
| 6,898,458 | B2 | 5/2005 | Zeng et al. |
| 6,960,165 | B2 | 11/2005 | Ueno et al. |
| 6,985,224 | B2 | 1/2006 | Hart |
| 6,999,173 | B2 | 2/2006 | Kleinfeld et al. |
| 7,075,628 | B2 | 7/2006 | Shepherd et al. |
| 7,094,562 | B2 | 8/2006 | Bittner |
| 7,096,124 | B2 | 8/2006 | Sterling et al. |
| 7,115,841 | B2 | 10/2006 | Zeng et al. |
| 7,133,545 | B2 | 11/2006 | Douglass et al. |
| 7,146,372 | B2 | 12/2006 | Bacus et al. |
| 7,149,332 | B2 | 12/2006 | Bacus et al. |
| 7,271,912 | B2 | 9/2007 | Sterling et al. |
| 7,279,134 | B2 | 10/2007 | Chan et al. |
| 7,303,922 | B2 | 12/2007 | Jeng et al. |
| 7,319,894 | B2 | 1/2008 | Higgins |
| 7,324,674 | B2 | 1/2008 | Ozawa et al. |
| 7,420,660 | B2 | 9/2008 | Muller et al. |
| 7,426,407 | B2 | 9/2008 | Higgins |
| 7,477,382 | B2 | 1/2009 | Grey et al. |
| 7,515,268 | B1 | 4/2009 | Ayliffe et al. |
| 7,518,727 | B2 | 4/2009 | Pentoney et al. |
| 7,539,335 | B2 | 5/2009 | Fukuyama |
| 7,560,073 | B1 | 7/2009 | Peters et al. |
| 7,625,712 | B2 | 12/2009 | Paul et al. |
| 7,630,063 | B2 | 12/2009 | Padmanabhan et al. |
| 7,674,598 | B2 | 3/2010 | Paul et al. |
| 7,738,094 | B2 | 6/2010 | Goldberg |
| 7,762,946 | B2 | 7/2010 | Sugimoto |
| 7,781,226 | B2 | 8/2010 | Mcdevitt et al. |
| 7,790,464 | B2 | 9/2010 | Tarasev |
| 7,816,135 | B2 | 10/2010 | Goldberg |
| 7,826,728 | B2 | 11/2010 | Konno et al. |
| 7,854,891 | B2 | 12/2010 | Yamamoto et al. |
| 7,892,551 | B2 | 2/2011 | Glencross |
| 7,903,241 | B2 | 3/2011 | Wardlaw et al. |
| 7,952,692 | B2 | 5/2011 | Primack et al. |
| 8,009,894 | B2 | 8/2011 | Lindberg et al. |
| 8,125,623 | B2 | 2/2012 | Munger et al. |
| 8,224,058 | B2 | 7/2012 | Lindberg et al. |
| 8,244,021 | B2 | 8/2012 | Lett et al. |
| 8,306,594 | B2 | 11/2012 | Paseman et al. |
| 8,353,848 | B2 | 1/2013 | Long et al. |
| 8,377,398 | B2 | 2/2013 | Mcdevitt et al. |
| 8,406,859 | B2 | 3/2013 | Zuzak et al. |
| 8,483,789 | B2 | 7/2013 | Higgins |
| 8,488,903 | B2 | 7/2013 | Higuchi |
| 8,541,227 | B2 | 9/2013 | Christensen et al. |
| 2003/0152927 | A1 | 8/2003 | Jakobsen et al. |
| 2003/0170613 | A1 | 9/2003 | Straus |
| 2003/0175947 | A1 | 9/2003 | Liu et al. |
| 2003/0230728 | A1 | 12/2003 | Dai et al. |
| 2004/0115831 | A1 | 6/2004 | Meathrel et al. |
| 2004/0125370 | A1 | 7/2004 | Montagu |

(56) References Cited

U.S. PATENT DOCUMENTS

2004/0189311 A1 9/2004 Glezer et al.
2004/0191124 A1 9/2004 Noetzel et al.
2004/0224329 A1 11/2004 Gjerde et al.
2005/0142565 A1 6/2005 Samper et al.
2005/0190058 A1 9/2005 Call
2006/0024756 A1 2/2006 Tibbe et al.
2006/0183236 A1 8/2006 Berlin et al.
2006/0227325 A1 10/2006 Rulison et al.
2006/0241495 A1 10/2006 Kurtz
2006/0252079 A1 11/2006 Oldham et al.
2007/0132994 A1 6/2007 Kobayashi et al.
2007/0178009 A1 8/2007 Sakaino et al.
2008/0190220 A1 8/2008 Backes et al.
2008/0203319 A1 8/2008 Pentoney et al.
2008/0268469 A1 10/2008 Srienc et al.
2009/0075324 A1 3/2009 Pettersson
2009/0181411 A1 7/2009 Battrell et al.
2009/0317806 A1 12/2009 Hasson
2010/0291599 A1 11/2010 Tague, Jr. et al.
2011/0102768 A1 5/2011 Dosmann et al.
2011/0118139 A1* 5/2011 Mehta .................. C12Q 1/6874 506/9
2012/0040470 A1 2/2012 Dorn et al.
2012/0194805 A1 8/2012 Ness et al.
2013/0041236 A1 2/2013 Pugia et al.
2013/0045529 A1 2/2013 Goldberg et al.
2013/0162990 A1 6/2013 Kobayashi et al.
2014/0200154 A1 7/2014 Sugarman et al.
2015/0132789 A1 5/2015 Bornheimer et al.

FOREIGN PATENT DOCUMENTS

EP 0788615 A1 8/1997
EP 0821784 B1 11/1998
EP 0959346 A2 11/1999
EP 0663070 B1 5/2000
EP 0681177 B1 7/2000
EP 0744600 B1 8/2001
EP 0818682 B1 10/2001
EP 0809807 B1 7/2002
EP 0800074 B1 7/2003
EP 0969279 B1 10/2003
EP 1347702 A2 10/2003
EP 1456649 B1 7/2006
EP 1701150 A1 9/2006
EP 1324021 B1 1/2008
EP 1924195 A2 5/2008
EP 1990638 A1 11/2008
EP 2041549 4/2009
EP 2083687 A1 8/2009
EP 1405073 B1 3/2010
EP 2232442 A1 9/2010
EP 1698883 B1 1/2011
EP 2016390 B1 4/2013
EP 2605020 A2 6/2013
EP 1558934 B1 7/2013
JP 2000292354 A 10/2000
JP 2001088098 A3 4/2001
JP 2002-506208 A 2/2002
JP 2002-516982 6/2002
JP 2006515065 A 5/2006
WO WO 94/09366 A1 4/1994
WO WO 97/14951 A1 4/1997
WO WO 99/20998 A1 4/1999
WO WO 99/45384 A1 9/1999
WO 00/29847 A2 5/2000
WO WO 00/28297 A2 5/2000
WO WO 02/44729 A1 6/2002
WO WO 02/50518 A2 6/2002
WO WO 03/036290 A1 5/2003
WO 2004017374 A2 2/2004
WO 2004/100887 A2 11/2004
WO 2005100539 A2 10/2005
WO WO 2006047831 A1 5/2006
WO WO 2006/096126 A1 9/2006
WO WO 2006/116616 A2 11/2006
WO WO 2006/119368 A2 11/2006
WO WO2007012975 A1 2/2007
WO WO 2007033318 A2 3/2007
WO WO 2007/051861 A1 5/2007
WO WO 2007/111555 A1 10/2007
WO WO 2008/002462 A2 1/2008
WO WO 2008/010761 A1 1/2008
WO WO 2008037068 A1 4/2008
WO WO 2008/103992 A2 8/2008
WO WO 2008/137212 A1 11/2008
WO WO 2009/091318 A1 7/2009
WO WO 2009/105711 A1 8/2009
WO WO 2009/125998 A2 10/2009
WO WO 2010/085658 A1 7/2010
WO WO 2011/133540 A2 10/2011
WO WO 2013/075031 A1 5/2013

OTHER PUBLICATIONS

Fridley et al., Controlled release of dry reagents in porous media for tunable temporal and spatial distribution upon rehydration, Lab Chip. Nov. 7, 2012;12(21):4321-4327.
Bornheimer et al., "Development of the BD FACSPresto™ System for Point-of-Care Determination of CD4 absolute count %CD4, and total Hb", BD Biosciences IAS FACSPresto Poster (2013), 1 page.
Beach, J. M. "A LED light calibration source for dual-wavelength microscopy," Cell Calcium, 21 (1): 63-68 (1997).
Cheng et al. "A microfluidic device for practical label-free CD4+ T cell counting of HIV-infected subjects," Lab Chip, 7: 170-178 (2007).
Debernardi et al. "Single cell Ca2+ /cAMP cross-talk monitoring by simutaneous Ca2+ /cAMP fluorescence ratio imaging," Proc. Natl. Acad. Sci. 93:4577-4582 (1996).
Fischer et al. "An affordable, portable fluorescent imaging device for skin lesion detection using a dual wavelength approach for image contrast enhancement and aminolaevulinic acid-induced protoporphyrin IX. Part I. Design, spectral and spatial characteristics," Lasers Med Sci., 16: 199-296 (2001).
Fischer et al. "An affordable, portable fluorescent imaging device for skin lesion detection using a dual wavelength approach for image contrast enhancement and aminolaevulinic acid-induced protoporphyrin IX. Part II. In vivo testing," Lasers Med Sci., 16: 207-212 (2001).
Gerstner et al. "Quantitative Histology by Multicolor Slide-based Cytometry," Cytometry Part A, 50A: 210-219 (2004).
Hart et al. "Light emitting diode excitation emission matrix fluorescence spectroscopy," Anlayst. (127): 1693-1699 (2002).
Heiden et al. "New Epi-Fluorescence optical system for independent analysis of two different fluorochromes in microscopy," Cytometry 20: 95-101 (1995).
Holland et al. "Point-of-care molecular diagnostic systems—past, present and future," Current Opinion in Microbiology, 8: 504-509 (2005).
Janossy et al. " Precise CD4 T-Cell counting using red diode laser excitation: for richer, for poorer," Cytometry (Clinical Cytometry) 50: 78-85 (2002).
Kassotis et al. "An inexpensive dual-excitation apparatus for fluorescence microscopy," Pfugers Arch., 409:47-51 (1987).
Lewis et al. "Color-blind fluorescence detection for four-color DNA sequencing"; PNAS; www.pnas.org/cgi/ doi/10/1073/pnas.0501606102; Apr. 12, 2005; vol. 102, No. 5: 5346-5351.
Li et al. "CD4 T lymphocytes enumeration by an easy-to-use single platform Image cytometer for HIV monitoring in resource-constrained settings," Cytometry Part B (Clinical Cytometry) 728: 397-407 (2007).
Myers et al. "Innovations in optical microfluidic technologies for point-of-care diagnostics", Lab on a Chip, vol. 8, pp. 2015-2031 (2008).
Rodriguez et al. "A microchip CD4 counting method for HIV monitoring in resource-poor settings," PLoS Medicine, 2 (7): 0663-0672 (2005).

(56) References Cited

OTHER PUBLICATIONS

Shapiro, "Cellular astronomy—a foreseeable future in cytometry," Cytometry Part A, 60A: 115-124 (2004).
Shapiro, "Personal cytometers: Slow flow or no flow,"Cytometry Part A, 69A: 620-630 (2006).
Fukano et al. "Fast dual-excitation radiometry with light-emitting diodes and high-speed liquid crystal shutters," Biochemical and Biophysical Research Communications, 340:250-255 (2006).
Toner et al. "Blood-on-a-chip," Annu. Rev. Biomed. Eng. 7: 77-103 (2005).
Tsien et al. "Measurement of cytosolic free Ca2+ in individual small cells using fluorescence microscopy with dual excitation wavelengths," Cell Calcium 6:145-157 (1985).
Warner et al. "Multicomponent analysis in clinical chemistry by use of rapid scanning fluorescence spectroscopy," Clin. Chern. 22/9: 1483-1492 (1967).
Wittrup et al. "Fluorescence array detector for large-field quantitative fluorescence cytometry," Cytometry 16: 206-213 (1994).
Yager et al. "Microfluidic diagnostic technologies for global public health," Nature 442: 412-418 (2006).
Ymeti et al. "A single platform image cytometer for resource-poor settings to monitor disease progression in HIV infection," Cytometry Part A 71A: 132-142 (2007).
Malmstadt et al. "'Smart' mobile affinity matrix for microfluidic immunoassays," Lab on a Chip 2004, vol. 4, pp. 412-415.
Tsougeni et al. "'Smart' polymeric microfluidics fabricated by plasma processing: controlled wetting, capillary filling and hydrophobic valving," Lab on a Chip 2010, vol. 10, pp. 462-469.
Anonymous: "Absorbance—Wikipedia, the free encyclopedia," Oct. 23, 2013, Retrieved from the Internet: URL: https://web.archive.org/web/20131023072058/https://en.wikipedia.org/wiki/Absorbance [retrieved on Jun. 20, 2017], 5 pages.
Anonymous: "Beer-Lambert law—Wikipedia, the free encyclopedia," May 26, 2013, Retrieved from the Internet: URL: https://web.archive.org/web/20130526203223/https://en.wikipedia.org/wiki/Beer-Lambert_law [retrieved on Jun. 20, 2017], 6 pages.

* cited by examiner

MICROFLUIDIC DEVICES, AND METHODS OF MAKING AND USING THE SAME

CROSS-REFERENCE TO RELATED APPLICATIONS

This application is related to U.S. Provisional Patent Application Ser. No. 61/900,590, filed Nov. 6, 2013, the disclosure of which application is incorporated herein by reference.

INTRODUCTION

Point-of-care diagnosis includes the steps of obtaining a biological sample from a subject, performing sample analysis to determine the presence or concentration of one or more target analytes and providing a diagnosis to the subject at a single location. Point-of care diagnosis provide quicker and often less costly results to the subject than diagnostic testing which requires obtaining a sample at one location and performing sample analysis at a different location.

Rapid diagnosis of infectious diseases from a single finger-stick blood drop using an inexpensive and facile technology available at the point-of-care would greatly improve global health initiatives. Flow cytometry-based micro-particle immunoassays provide excellent accuracy and multiplexing, but are inappropriate for point-of-care settings due to cumbersome sample preparation and expensive instrumentation. In view of the above, several medical and biotechnology fields would be significantly advanced with the availability of techniques capable of point-of-care operation, which permitted facile and flexible measurements of cellular markers, particularly in biological fluids, such as blood.

SUMMARY

Aspects of the present disclosure include a microfluidic device for assaying a sample. Microfluidic devices according to certain embodiments include a sample application site, a flow channel in fluid communication with the sample application site and a porous component that contains a porous matrix and assay reagent positioned between the sample application site and the flow channel. Systems and methods suitable for assaying a sample, such as a biological sample, employing the subject microfluidic devices are also described.

As summarized above, aspects of the present disclosure include a microfluidic device for assaying a sample having a sample application site, a flow channel in fluid communication with the application site and a porous component positioned between the sample application site and the flow channel. In embodiments, the porous component includes a porous matrix and an assay reagent. In some instances, the porous matrix is a frit, such as a glass frit. In other instances, the porous matrix is a polymeric matrix. In some embodiments, the porous matrix is configured to be non-filtering with respect to components of the sample. In certain instances, the porous matrix is configured to provide for mixing of the assay reagent with the sample flowing through the porous matrix. The porous matrix may have pores having diameters of between 1 μm and 200 μm and pore volumes of between 1 μL and 25 μL. For example, the pore volume may be between 25% and 75% of the volume of the porous matrix, such as between 40% and 60% of the volume of the porous matrix.

The assay reagent includes a reagent for coupling to one or more components of the sample. In some embodiments, the reagent is an analyte-specific binding member. For example, the analyte-specific binding member may be an antibody or antibody fragment. In certain instances, the analyte-specific binding member is an antibody that binds specifically to a compound such as CD14, CD4, CD45RA, CD3 or a combination thereof. In some embodiments, the analyte-specific binding member is coupled to a detectable label, such as an optically detectable label. For instance, the optically detectable label may be a fluorescent dye such as of rhodamine, coumarin, cyanine, xanthene, polymethine, pyrene, dipyrromethene borondifluoride, napthalimide, phycobiliprotein, peridinium chlorophyll proteins or a combination thereof. In certain instances, the dye is phycoerythrin (PE), Phycoerythrin Cyanine 5, (PE-cy5) or Allophycocyanin APC. In some embodiments, buffers include bovine serum albumin (BSA), trehalose, polyvinylpyrrolidone (PVP) or 2-(N-morpholino) ethanesulfonic acid or a combination thereof. For instance, the buffer may include BSA, trehalose and PVP. Buffers may also include one or more chelating agents, such as ethylene diamine tetra acetic acid (EDTA), ethyleneglycol-bis-(beta-aminoethyl ether) N,N,N',N'-tetraacetic acid (EGTA), 2,3-dimercaptopropanel-1-sulfonic acid (DMPS), and 2,3-dimercaptosuccinic acid (DMSA). In certain embodiments, the buffer includes EDTA. The assay reagent may be present in the porous matrix as a liquid. In other instances, the assay reagent is dry. In yet other instances, the assay reagent is lyophilized.

In some embodiments, the flow channel is configured to receive a sample having a volume ranging from 1 mL to 1000 mL. In certain instances, the flow channel is a capillary channel configured to transport the sample through the flow channel by capillary action. In certain embodiments, the flow channel includes one or more optically transmissive walls. In one example, the flow channel is optically transmissive to ultraviolet light. In another example, the flow channel is optically transmissive to visible light. In yet another example, the flow channel is optically transmissive to near-infrared light. In still another example, the flow channel is transmissive to ultraviolet light and visible light. In still another example, the flow channel is transmissive to visible light and near-infrared light. In still another example, the flow channel is transmissive to ultraviolet light, visible light and near-infrared light.

Microfluidic devices according to certain embodiments include a porous frit that contains microchannels defining a tortuous flow-path having a length sufficient for the mixing of a reagent and a sample. The pore volume may be 40 to 60% of the total volume of the porous frit such as 2 μL or more, such as 5 μL, 10 μL and including 20 μL or more. In some embodiments the microchannels provide for the flow through of substantially all components of the sample. In some embodiments the microchannels have an average through-pore diameter between 5 μm and 200 μm such as between 5 μm and 60 μm or between 30 μm and 60 μm.

The assay mixture includes a reagent and buffer. In some instances, the assay mixture provides for the substantially uniform dissolution of the reagent into the sample over a predetermined period of time. The predetermined period of time may be between 5 seconds and 5 minutes such as between 20 seconds and 3 minutes or between 50 seconds and 2 minutes. In some embodiments, the buffer components include bovine serum albumin (BSA), trehalose, and polyvinylpyrrolidone (PVP). The weight ratio of BSA:Trehalose:PVP may be 21:90:1. The total weight of buffer components may be between 0.01 g/μL and 2 g/μL of the porous matrix pore volume. In some embodiments the buffer components includes ethylenediaminetetraacetic acid (EDTA). In certain embodiments, the buffer components comprise 2-(N-morpholino) ethanesulfonic acid (MES). In some instances, the reagent includes one or more antibody or antibody fragments conjugated to a detectable label. The antibody or antibody fragments may bind to a target, such as a target selected from CD14, CD4, CD45RA, CD3 or a combination thereof. In some instances, the detectable label is a fluorescent dye. For example, the dye may be a compound such as rhodamine, coumarin, cyanine, xanthene, polymethine, pyrene, dipyrromethene borondifluoride, napthalimide, phycobiliprotein, peridinium chlorophyll proteins, conjugates thereof, and combinations thereof. In some embodiments the dye may be phycoerythrin (PE), Phycoerythrin Cyanine 5, (PE-cy5) or Allophycocyanin APC. In embodiments of the present disclosure, the assay mixture may include enzymes, substrates, catalysts, nucleic acids or a combination thereof. In certain instances, microfluidic devices may further include a biological sample such as blood, urine, saliva, or a tissue sample.

Aspects of the present disclosure also include a method for assaying a sample for an analyte where the method includes contacting a sample to a sample application site of a microfluidic device having a flow channel in fluid communication with the sample application site and a porous component positioned between the sample application site and the flow channel, illuminating the sample in the flow channel with a light source and detecting light from the sample to determine the presence or concentration of one or more components in the sample.

In some embodiments, the sample mixes with an assay reagent present in the porous matrix of the porous component by movement of the sample through the porous matrix. Movement of the sample through the porous matrix is, in certain embodiments, non-filtering with respect to components of the sample. In some embodiments, the flow channel is a capillary channel and sample is moved through the porous matrix by capillary action. Mixing of the sample with the assay reagent may include labeling one or more components of the sample with a detectable label. In some instances, labelling includes contacting one or more components of the sample with an analyte-specific binding member, such as an antibody or antibody fragment. In certain instances, the analyte-specific binding member is an antibody that binds specifically to a compound such as CD14, CD4, CD45RA, CD3 or a combination thereof. In some embodiments, the analyte-specific binding member is coupled to a detectable label, such as an optically detectable label. Examples of optically detectable labels include fluorescent dyes such as rhodamine, coumarin, cyanine, xanthene, polymethine, pyrene, dipyrromethene borondifluoride, napthalimide, phycobiliprotein, peridinium chlorophyll proteins, conjugates thereof, and combinations thereof. In some embodiments, the dye is phycoerythrin (PE), Phycoerythrin Cyanine 5, (PE-cy5) or Allophycocyanin APC.

Methods according to some embodiments include illuminating the sample in the flow channel with a broad spectrum light source. In some embodiments, the broad spectrum light source is an ultraviolet light source, a visible light source or an infrared light source, or a combination thereof. In certain embodiments, the sample is illuminated with light having a wavelength between 200 nm and 800 nm.

In some embodiments, methods also include detecting light from the sample in the flow channel. Light detected from the sample may include fluorescence, transmitted light, scattered light or a combination thereof. In some instances, methods include detecting fluorescence from the sample. In certain instances, detecting light from the sample include capturing an image of the sample in the flow channel.

Methods for assaying a sample, such as a biological sample, with the subject microfluidic devices are also provided. In some embodiments, methods include applying a liquid sample to a sample application site that is in fluid communication with a porous element and a capillary channel, directing the sample flow from the sample application site, through the porous element, to the capillary channel. The capillary channel may include an optically transmissive wall and the porous element includes at least one optically active reagent and one or more buffer components.

Methods may further include dissolving the reagent in the sample where dissolution of the reagent is substantially constant over a predetermined amount of time, such as between 5 seconds and 5 minutes or as between 20 seconds and 3 minutes or between 1 minute and 2 minutes. In some embodiments, mixing of the sample and the reagent is performed in a porous frit that provides a series of microchannels defining a tortuous flow-path having a length sufficient for mixing the sample and reagent. The mixing may facilitate the binding of the reagent to one or more components in the sample and is followed by optically interrogating the sample through the optically transmissive wall. The mixing may be passive (diffusive), convective, active or any combination thereof. The sample may flow by a capillary action force through the porous element and through the capillary channel. In certain embodiments, optical interrogation includes obtaining an image of the sample through a transmissive wall, determining a background signal that corresponds to unbound reagent and sample and subtracting the background signal from the image of the sample. In some embodiments, the background signal is substantially constant (varies by 75% or less, such as by 50%) along the transmissive wall. In some instances, the sample flows through the porous element substantially unfiltered. In embodiments, the sample may be a biological sample, such as blood, urine, tissue, saliva or the like. In some embodiments, the optically active reagent includes a fluorescently labeled antibody or antibody fragment and the mixing provides for the formation of one or more fluorescently labeled component in the biological sample.

Aspects of the present disclosure also include systems for practicing the subject methods. Systems according to certain embodiments, include a light source, an optical detector for detecting one or more wavelengths of light and a microfluidic device for assaying a sample having a sample application site, a flow channel in fluid communication with the application site and a porous component positioned between the sample application site and flow channel.

Definition of Select Terminology

Generally, terms used herein not otherwise specifically defined have meanings corresponding to their conventional usage in the fields related to the invention, including analytical chemistry, biochemistry, molecular biology, cell biology, microscopy, image analysis, and the like, such as represented in the following treatises: Alberts et al, Molecular Biology of the Cell, Fourth Edition (Garland, 2002); Nelson and Cox, Lehninger Principles of Biochemistry, Fourth Edition (W.H. Freeman, 2004); Murphy, Fundamentals of Light Microscopy and Electronic Imaging (Wiley-Liss, 2001); Shapiro, Practical Flow Cytometry, Fourth Edition (Wiley-Liss, 2003); Owens et al (Editors), Flow Cytometry Principles for Clinical Laboratory Practice:

Quality Assurance for Quantitative Immunophenotyping (Wiley-Liss, 1994); Ormerod (Editor) Flow Cytometry: A Practical Approach (Oxford University Press, 2000); and the like.

"Antibody" or "immunoglobulin" means a protein, either natural or synthetically produced by recombinant or chemical means, that is capable of specifically binding to a particular antigen or antigenic determinant. Antibodies are usually heterotetrameric glycoproteins of about 150,000 Daltons, composed of two identical light (L) chains and two identical heavy (H) chains. "Antibody fragment", and all grammatical variants thereof, as used herein are defined as a portion of an intact antibody comprising the antigen binding site or variable region of the intact antibody, wherein the portion is free of the constant heavy chain domains (i.e., CH2, CH3, and CH4, depending on antibody isotype) of the Fc region of the intact antibody. Examples of antibody fragments include Fab, Fab', Fab'-SH, $F(ab')_2$, and Fv fragments. The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by Hybridoma culture, uncontaminated by other immunoglobulins. Guidance in the production and selection of antibodies for use in immunoassays can be found in readily available texts and manuals, e.g., Harlow and Lane, Antibodies: A Laboratory Manual (Cold Spring Harbor Laboratory Press, New York, 1988); Howard and Bethell, Basic Methods in Antibody Production and Characterization (CRC Press, 2001); Wild, editor, The Immunoassay Handbook (Stockton Press, New York, 1994), and the like.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, e.g., to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g., having maximal cross-sectional dimensions of from about 500 μm to about 0.1 μm. Microfluidics devices typically have volume capacities in the range of from 1 μL to a fewer than 10 nL, e.g., 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437.

"Sample" means a quantity of material from a biological, environmental, medical, or patient source in which detection or measurement of predetermined cells, particles, beads, and/or analytes is sought. A sample may comprise material from natural sources or from man-made sources, such as, tissue cultures, fermentation cultures, bioreactors, and the like. Samples may comprise animal, including human, fluid, solid (e.g., stool) or tissue, as well as liquid and solid food and feed products and ingredients such as dairy items, vegetables, meat and meat by-products, and waste. Samples may include materials taken from a patient including, but not limited to, cultures, blood, saliva, cerebral spinal fluid, pleural fluid, milk, lymph, sputum, semen, needle aspirates, and the like. Samples may be obtained from all of the various families of domestic animals, as well as feral or wild animals, including, but not limited to, such animals as ungulates, bear, fish, rodents, etc. Samples may include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. The terms "sample," "biological sample," and "specimen" are used interchangeably.

BRIEF DESCRIPTION OF THE FIGURES

The invention may be best understood from the following detailed description when read in conjunction with the accompanying drawings. Included in the drawings are the following figures:

FIG. 2 panel B depicts a schematic showing the side view of a microfluidic device according to certain embodiments.

FIG. 3 panel B depicts an illustration of imaging enhancement of components of a sample in the microfluidic device according to certain embodiments.

DETAILED DESCRIPTION

Figure 1:
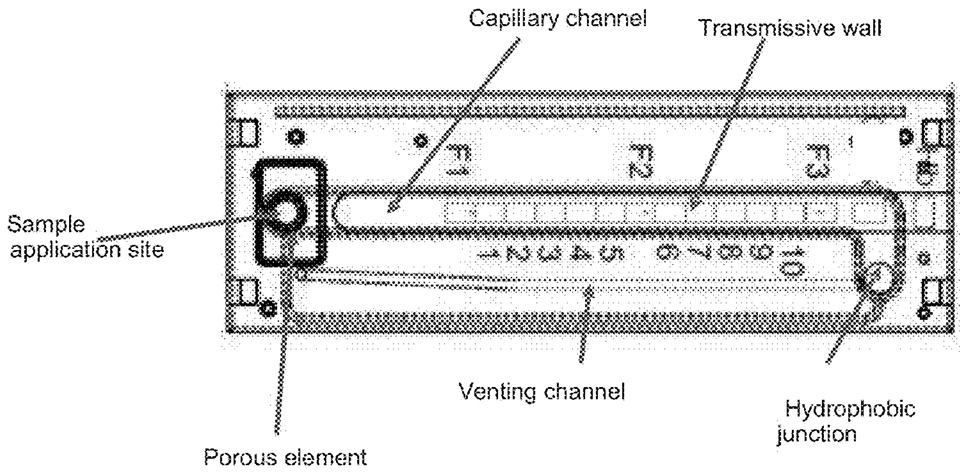
FIG. 1 depicts an illustration from a top view of a microfluidic device according to certain embodiments.

A microfluidic device and method for using the same are described. The device may include a sample application site in communication with a porous component and a flow channel. The dimensions of the device may provide for capillary action to be the primary force for transmitting a sample through the porous element and the flow channel. The device may be used to interrogate analytes or components in a sample that have been labeled with a detectable label. The porous component is comprised of a porous matrix, such as a frit and an assay reagent. The porous component may provide a matrix for the assay reagent and have sufficient dimensions to provide a tortuous path for the mixing of sample and an assay reagent. The mixing may be passive or convective and require no additional force beyond the capillary force to provide for a sample that is substantially uniformly mixed with an assay reagent upon exit from the porous matrix. The assay reagent may provide for the uniform dissolution of a reagent such as a detectable label into the sample over a defined period of time.

The practice of the present invention may employ, unless otherwise indicated, conventional techniques from molecular biology (including recombinant techniques), cell biology, immunoassay technology, microscopy, image analysis, and analytical chemistry, which are within the skill of the art. Such conventional techniques include, but are not limited to, detection of fluorescent signals, image analysis, selection of illumination sources and optical signal detection components, labeling of biological cells, and the like. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press); Murphy, Fundamentals of Light Microscopy and Electronic Imaging (Wiley-Liss, 2001); Shapiro, Practical Flow Cytometry, Fourth Edition (Wiley-Liss, 2003); Herman et al, Fluorescence Microscopy, 2nd Edition (Springer, 1998); the disclosures of which are herein incorporated in their entirety by reference for all purposes.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, aspects of the present disclosure include a microfluidic device for assaying a sample. In further describing embodiments of the disclosure, microfluidic devices of interest are first described in greater detail. Next, methods for assaying a sample employing the subject microfluidic devices are described. Systems suitable for practicing the subject methods to assay a sample for an analyte are described. Kits are also provided.

Microfluidic Devices

As summarized above, aspects of the present disclosure include a microfluidic device for assaying a sample for one or more analytes. The term "assaying" is used herein in its conventional sense to refer to qualitatively assessing the presence or quantitatively measuring an amount of a target analyte species in the sample. As described in greater detail below, a variety of different samples may be assayed with the subject microfluidic device. In some instances, the sample is a biological sample. The term "biological sample" is used in its conventional sense to include a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may include any type of organismic material, including both healthy and diseased components (e.g., cancerous, malignant, necrotic, etc.). In certain embodiments, the biological sample is a liquid sample, such as whole blood or derivative thereof, plasma, tears, sweat, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. Biological samples of interest may be obtained from human subjects of both genders and at any stage of development (i.e., neonates, infant, juvenile, adolescent, adult), where in certain embodiments the human subject is a juvenile, adolescent or adult. While the present disclosure may be applied to samples from a human subject, it is to be understood that microfluidic devices may also be employed with samples from other non-human animal subjects such as, but not limited to, birds, mice, rats, dogs, cats, livestock and horses.

In embodiments of the present disclosure, microfluidic devices include a sample application site, a flow channel in fluid communication with the sample application site and a porous component that contains a porous matrix and an assay reagent positioned between the sample application site and flow channel. The sample application site of the microfluidic device is a structure configured to receive a sample having a volume ranging from 5 μL to 1000 μL, such as from 10 μL to 900 μL, such as from 15 μL to 800 μL, such as from 20 μL to 700 μL, such as from 25 μL to 600 μL, such as from 30 μL to 500 μL, such as from 40 μL to 400 μL, such as from 50 μL to 300 μL and including from 75 μL to 250 μL. The sample application site may be any convenient shape, so long as it provides for fluid access, either directly or through an intervening component that provides for fluidic communication, to the flow channel. In some embodiments, the sample application site is planar. In other embodiments, the sample application site is concave, such as in the shape of an inverted cone terminating at the sample inlet orifice. Depending on the amount of sample applied and the shape of the sample application site, the sample application site may have a surface area ranging from 0.01 $mm^2$ to 1000 $mm^2$, such as from 0.05 $mm^2$ to 900 $mm^2$, such as from 0.1 $mm^2$ to 800 $mm^2$, such as from 0.5 $mm^2$ to 700 $mm^2$, such as from 1 $mm^2$ to 600 $mm^2$, such as from 2 $mm^2$ to 500 $mm^2$ and including from 5 $mm^2$ to 250 $mm^2$.

The inlet of the microfluidic device is in fluidic communication with sample application site and the flow channel and may be any suitable shape, where cross-sectional shapes of inlets of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. The dimensions of the nozzle orifice may vary, in some embodiments ranging from 0.01 mm to 100 mm, such as from 0.05 mm to 90 mm, such as from 0.1 mm to 80 mm, such as from 0.5 mm to 70 mm, such as from 1 mm to 60 mm, such as from 2 mm to 50 mm, such as from 3 mm to 40 mm, such as from 4 mm to 30 mm and including from 5 mm to 25 mm. In some embodiments, the inlet is a circular orifice and the diameter of the inlet ranges from 0.01 mm to 100 mm, such as from 0.05 mm to 90 mm, such as from 0.1 mm to 80 mm, such as from 0.5 mm to 70 mm, such as from 1 mm to 60 mm, such as from 2 mm to 50 mm, such as from 3 mm to 40 mm, such as from 4 mm to 30 mm and including from 5 mm to 25 mm. Accordingly, depending on the shape of the inlet, sample inlet orifice may have an opening which varies, ranging from 0.01 $mm^2$ to 250 $mm^2$, such as from 0.05 $mm^2$ to 200 $mm^2$, such as from 0.1 $mm^2$ to 150 $mm^2$, such as from 0.5 $mm^2$ to 100 $mm^2$, such as from 1 $mm^2$ to 75 $mm^2$, such as from 2 $mm^2$ to 50 $mm^2$ and including from 5 $mm^2$ to 25 $mm^2$.

In embodiments, the sample inlet is in fluid communication with a porous component that contains a porous matrix and an assay reagent positioned between the sample application site and flow channel. By "porous matrix" is meant a substrate which contains one or more pore structures configured for the permeation of liquid components therethrough. In some embodiments, the porous matrix contains a network of interconnected pores that provides a medium for mixing an applied sample (e.g., a biological sample as discussed in greater detail below) with an assay reagent present in the porous matrix. In other embodiments, the porous matrix contains a network of interconnected pores that is non-filtering to the sample. By "non-filtering" is meant that the network of interconnected pores does not substantially restrict the passage of components of the sample through the porous matrix (i.e., to the flow channel), such as where passage of 1% or less of sample components is restricted by the pores of the porous matrix, such as 0.9% or less, such as 0.8% or less, such as 0.7% or less, such as 0.5% or less, such as 0.1% or less, such as 0.05% or less, such as 0.01% or less, such as 0.001% or less and including where 0.0001% or less of the sample components are restricted by the pores of the porous matrix. In other words, 1% or less of the sample remains in the porous matrix after passage of the sample, such as 0.9% or less, such as 0.8% or less, such as 0.7% or less, such as 0.5% or less, such as 0.1% or less, such as 0.05% or less, such as 0.01% or less, such as 0.001% or less and including 0.0001% or less of the sample remains in the porous matrix after passage of the sample. Put another way, porous matrices of interest include a network of interconnected pores which is configured to provide for passage of substantially all of the sample through the porous matrix, such as where 99% or more of the sample passes through the porous matrix, such as 99.5% or more, such as 99.9% or more, such as 99.99% or more, such as 99.999% or more and including passage of 99.9999% or more of the sample through the porous matrix. In certain embodiments, all (i.e., 100%) of the sample passes through the porous matrix.

The porous matrix positioned between the sample application site and the flow channel may be any suitable shape, such as planar polygonal shapes including but not limited to a circle, oval, half-circle, crescent-shaped, star-shaped, square, triangle, rhomboid, pentagon, hexagon, heptagon, octagon, rectangle or other suitable polygon. In other embodiments, porous matrices of interest are three-dimensional, such as in the shape of a cube, cone, half sphere, star, triangular prism, rectangular prism, hexagonal prism or other suitable polyhedron. In certain embodiments, the porous matrix is disk-shaped. In other embodiments, the porous matrix is cylindrical. The dimensions of the porous matrix may vary, in some embodiments ranging from 0.01 mm to 100 mm, such as from 0.05 mm to 90 mm, such as from 0.1 mm to 80 mm, such as from 0.5 mm to 70 mm, such as from 1 mm to 60 mm, such as from 2 mm to 50 mm, such as from 3 mm to 40 mm, such as from 4 mm to 30 mm and including from 5 mm to 25 mm. In some embodiments, the porous matrix is a circular and the diameter of the porous matrix ranges from 0.01 mm to 100 mm, such as from 0.05 mm to 90 mm, such as from 0.1 mm to 80 mm, such as from 0.5 mm to 70 mm, such as from 1 mm to 60 mm, such as from 2 mm to 50 mm, such as from 3 mm to 40 mm, such as from 4 mm to 30 mm and including from 5 mm to 25 mm and has a height from 0.01 mm to 50 mm, such as from 0.05 mm to 45 mm, such as from 0.1 mm to 40 mm, such as from 0.5 mm to 35 mm, such as from 1 mm to 30 mm, such as from 2 mm to 25 mm, such as from 3 mm to 20 mm, such as from 4 mm to 15 mm and including from 5 mm to 10 mm.

Pore sizes of the porous matrix may also vary, depending on the biological sample and assay reagents present and may range from 0.01 μm to 200 μm, such as from 0.05 μm to 175

μm, such as 0.1 μm to 150 μm, such as 0.5 μm to 125 μm, such as 1 μm to 100 μm, such as 2 μm to 75 μm and including 5 μm to 50 μm. In embodiments, the porous matrix may have a pore volume sufficient to contain all or part of the applied sample as desired. For example, 50% or more of the sample volume may fit within the porous matrix, such as 55% or more, such as 60% or more, such as 65% or more, such as 75% or more, such as 90% or more, such as 95% or more, such as 97% or more and including 99% or more of the sample volume may fit within the porous matrix. In certain embodiments, the porous matrix has a pore volume that is sufficient to contain all (i.e., 100%) of the sample. For instance, the pore volume of the porous matrix may range from 0.01 μL to 1000 μL, such as from 0.05 μL to 900 μL, such as 0.1 μL to 800 μL, such as 0.5 μL to 500 μL, such as 1 μL to 250 μL, such as 2 μL to 100 μL and including 5 μL to 50 μL. In embodiments, the void fraction (i.e., the ratio of void volume within the pores and the total volume) of porous matrices of interest ranges from 0.1 to 0.9, such as from 0.15 to 0.85, such as from 0.2 to 0.8, such as from 0.25 to 0.75, such as from 0.3 to 0.7, such as from 0.35 to 0.65 and including from 0.4 to 0.6. Put another way, the pore volume is from 10% and 90% of the total volume of the porous matrix, such as from 15% and 85%, such as from 20% and 80%, such as from 25% and 75%, such as from 30% and 70%, such as from 35% and 65% and including a pore volume from 40% and 60% of the total volume of the porous matrix.

In some embodiments, porous matrices of interest are configured to provide for a predetermined flow rate of the sample through the porous matrix. As discussed above, sample may be mixed with an assay reagent within the pores of the porous matrix and flow through the porous matrix to the flow channel by capillary action. In certain instances, the porous matrix is configured to provide for a flow rate through the porous matrix to the flow channel that is 0.0001 μl/min or more, such as 0.0005 μl/min or more, such as 0.001 μl/min or more, such as 0.005 μl/min or more, such as 0.01 μl/min or more, such as 0.05 μl/min or more, such as 0.1 μl/min or more, such as 0.5 μl/min or more, such as 1 μl/min or more, such as 2 μl/min or more, such as 3 μl/min or more, such as 4 μl/min or more, such as 5 μl/min or more, such as 10 μl/min or more, such as 25 μl/min or more, such as 50 μl/min or more, such as 100 μl/min and including a rate of flow through the porous matrix of 250 μl/min or more. For example, the porous matrix may be configured to pass the sample through the porous matrix (where the sample is mixed with assay reagent) at a rate ranging from 0.0001 μl/min to 500 μl/min, such as from 0.0005 μl/min to 450 μl/min, such as from 0.001 μl/min to 400 μl/min, such as from 0.005 μl/min to 350 μl/min, such as from 0.01 μl/min to 300 μl/min, such as from 0.05 μl/min to 250 μl/min, such as from 0.1 μl/min to 200 μl/min, such as from 0.5 μl/min to 150 μl/min and including passing the sample through the porous matrix at a rate from 1 μl/min to 100 μl/min.

In some embodiments, the subject porous matrices are configured to pass the sample through the porous matrix over a predetermined amount of time. For example, the porous matrix may have a pore structure where the sample passes through the porous matrix in an amount time such as over a duration of 5 seconds or more, such as over 10 seconds or more, such as over 30 seconds or more, such as over 60 seconds or more, such as over 2 minutes or more, such as over 3 minutes or more, such as over 5 minutes or more, such as over 10 minutes or more and including passing the sample through the porous matrix over a duration of 30 minutes or more. In certain instances, the porous matrix is configured to have a pore structure where the sample passes the through the porous matrix over a duration ranging from 1 second to 60 minutes, such as from 2 second to 30 minutes, such as from 5 seconds to 15 minutes, such as from 10 seconds to 10 minutes, such as from 15 seconds to 5 minutes and including from 20 seconds to 3 minutes.

The porous matrix may be any suitable macroporous or microporous substrate and include but are not limited to ceramic matrices, frits, such as fritted glass, polymeric matrices as well as metal-organic polymeric matrices. In some embodiments, the porous matrix is a frit. The term "frit" is used herein in its conventional sense to refer to the porous composition formed from a sintered granulated solid, such as glass. Frits may have a chemical constituent which vary, depending on the type of sintered granulate used to prepare the frit and may include but not limited to frits composed of aluminosilicate, boron trioxide, borophosphosilicate glass, borosilicate glass, ceramic glaze, cobalt glass, cranberry glass, fluorophosphate glass, fluorosilicate glass, fuzed quartz, germanium dioxide, metal and sulfide embedded borosilicate, leaded glass, phosphate glass, phosphorus pentoxide glass, phosphosilicate glass, potassium silicate, soda-lime glass, sodium hexametaphosphate glass, sodium silicate, tellurite glass, uranium glass, vitrite and combinations thereof. In some embodiments, the porous matrix is a glass frit, such as a borosilicate, aluminosilicate, fluorosilicate, potassium silicate or borophosphosilicate glass frit.

In some embodiments, the porous matrix is a porous organic polymer. Porous organic polymers of interest vary depending on the sample volume, components in the sample as well as assay reagent present and may include but are not limited to porous polyethylene, polypropylene, polytetrafluoroethylene (PTFE), polyvinylidene fluoride (PVDF), ethyl vinyl acetate (EVA), polycarbonate, polycarbonate alloys, polyurethane, polyethersulfone, copolymers and combinations thereof. For example, porous polymers of interest include homopolymers, heteropolymerc and copolymers composed of monomeric units such as styrene, monoalkylene allylene monomers such as ethyl styrene, α-methyl styrene, vinyl toluene, and vinyl ethyl benzene; (meth)acrylic esters such as methyl(meth)acrylate, ethyl (meth)acrylate, butyl(meth)acrylate, isobutyl(meth)acrylate, isodecyl(meth)acrylate, 2-ethylhexyl (meth)acrylate, lauryl (meth)acrylate, stearyl(meth)acrylate, cyclohexyl(meth) acrylate, and benzyl(meth)acrylate; chlorine-containing monomers such as vinyl chloride, vinylidenechloride, and chloromethylstyrene; acrylonitrile compounds such as acrylonitrile and methacrylonitrile; and vinyl acetate, vinyl propionate, n-octadecyl acrylamide, ethylene, propylene, and butane, and combinations thereof.

In some embodiments, the porous matrix is a metal organic polymer matrix, for example an organic polymer matrix that has a backbone structure that contains a metal such as aluminum, barium, antimony, calcium, chromium, copper, erbium, germanium, iron, lead, lithium, phosphorus, potassium, silicon, tantalum, tin, titanium, vanadium, zinc or zirconium. In some embodiments, the porous metal organic matrix is an organosiloxane polymer including but not limited to polymers of methyltrimethoxysilane, dimethyldimethoxysilane, tetraethoxysilane, methacryloxypropyltrimethoxysilane, bis(triethoxysilyl)ethane, bis(triethoxysilyl)butane, bis(triethoxysilyl)pentane, bis(triethoxysilyl) hexane, bis(triethoxysilyl)heptane, bis(triethoxysilyl) octane, and combinations thereof.

In embodiments of the present disclosure, the porous component also includes an assay reagent. In some embodiments, assay reagents are present within the pores of the porous matrix and are configured to mix with components of the applied sample as the sample passes through the porous matrix. Assay reagents of interest present in the porous component may include analyte-specific binding members, such as enzymes, antibodies, substrates, oxidizers, among other analyte-specific binding members. In certain instances, the analyte-specific binding member includes a binding domain. By "specific binding" or "specifically binds" is meant the preferential binding of a domain (e.g., one binding pair member to the other binding pair member of the same binding pair) relative to other molecules or moieties in a solution or reaction mixture. The specific binding domain may bind (e.g., covalently or non-covalently) to a specific epitope of an analyte of interest. In certain instances, the specific binding domain non-covalently binds to a target. For example coupling between the analyte-specific binding member and the target analyte may be characterized by a dissociation constant, such as dissociation constant of $10^{-5}$ M or less, $10^{-6}$ M or less, such as $10^{-7}$ M or less, including $10^{-8}$ M or less, e.g., $10^{-9}$ M or less, $10^{-19}$ M or less, $10^{-11}$ M or less, $10^{-12}$ M or less, $10^{-13}$ M or less, $10^{-14}$ M or less, $10^{-15}$ M or less and including $10^{-16}$ M or less.

Analyte-specific binding members may vary depending on the type of biological sample and components of interest and may include but are not limited to antibody binding agents, proteins, peptides, haptens, nucleic acids, oligonucleotides. In some embodiments, the analyte-specific binding member is an enzyme. Examples of enzymes may include but are not limited to horseradish peroxidase, pyruvate oxidase, oxaloacetate decarboxylase, creatinine amidohydrolase, creatine amidinohydrolase, sarcosine oxidase, malate dehydrogenase, lactate dehydrogenase, FAD, TPP, P-5-P, NADH, amplex red and combinations thereof.

In certain embodiments, the analyte-specific binding member is an antibody binding agent. The term "antibody binding agent" is used herein in it conventional sense to refer to polyclonal or monoclonal antibodies or antibody fragments that are sufficient to bind to an analyte of interest. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. In certain embodiments, the analyte-specific binding member is an antibody or antibody fragment that binds specifically to a compound such as cluster of differentiation 14 (CD14), cluster of differentiation 4 (CD4), cluster of differentiation 45 RA (CD45RA) and cluster of differentiation 3 (CD3) or a combination thereof.

In some embodiments, the analyte-specific binding member is coupled to a detectable label. Any suitable detectable label may be employed, including but not limited to radioactive labels, labels detectable by spectroscopy techniques such as nuclear magnetic resonance as well as optically detectable labels such as labels detectable by UV-vis spectrometry, infrared spectroscopy, transient absorption spectroscopy and emission spectroscopy (e.g., fluorescence, phosphorescence, chemiluminescence). In certain embodiments, the analyte-specific binding member is coupled to an optically detectable label. In one example, the optically detectable label is a fluorophore. Examples of fluorophores may include, but are not limited to, 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC(XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene or combinations thereof, among other fluorophores. In certain embodiments, the fluorophore is a fluorescent dye such as rhodamine, coumarin, cyanine, xanthene, polymethine, pyrene, dipyrromethene borondifluoride, napthalimide, phycobiliprotein, peridinium chlorophyll proteins, conjugates thereof or a combination thereof. As described in greater detail below, fluorophores may be detected by emission maxima, light scatter, extinction coefficient, fluorescence polarization, fluorescence lifetime or combinations thereof.

The amount of analyte-specific binding member present in the assay reagent may vary depending on volume and type of the applied sample. In some instances, the amount of analyte-specific binding member is sufficient to provide a concentration of analyte-specific binding member in the sample present in the flow channel of from 0.0001 μg/mL to 250 μg/mL, such as from 0.0005 μg/mL to 240 μg/mL, such as from 0.001 μg/mL to 230 μg/mL, such as from 0.005 μg/mL to 220 μg/mL, such as from 0.01 μg/mL to 210 μg/mL, such as from 0.05 μg/mL to 200 μg/mL, such as from 0.1 μg/mL to 175 μg/mL, such as from 0.5 μg/mL to 150 μg/mL and including an amount of analyte-specific binding member sufficient to provide a concentration of analyte-specific binding member in the sample present in the flow channel from 1 μg/mL to 100 μg/mL. For example, the dry weight of analyte-specific binding member present in the porous component may range from 0.001 ng to 500 ng, such as from 0.005 ng to 450 ng, such as from 0.01 ng to 400 ng, such as from 0.05 ng to 350 ng, such as from 0.1 ng to 300 ng, such as from 0.5 ng to 250 ng and including a dry mass of analyte-specific binding member from 1 ng to 200 ng.

In some embodiments, the porous component also includes one or more buffers. The term "buffer" is used in its conventional sense to refer to a compound which helps to stabilize (i.e., maintain) the composition, such as for example during dissolution of the assay reagent in the applied sample. Buffers of interest may contain, but are not limited to, proteins, polysaccharides, salts, chemical binders and combinations thereof. Encompassed by the invention are both liquid and dry buffer formats, e.g., aqueous compositions that include the below components or dehydrated versions thereof.

In some embodiments, buffers include polysaccharides, such as from example glucose, sucrose, fructose, galactose, mannitol, sorbitol, xylitol, among other polysaccharides. In some instances, buffers include a protein such as BSA. In yet other instances, buffers of interest in a chemical binder, including but not limited to low molecular weight dextrans, cyclodextrin, polyethylene glycol, polyethylene glycol ester polyvinylpyrollidone (PVP) or other hydrophilic polymers selected from the group consisting of hyaluronic acid, polyvinylpyrollidone (PVP), copolymers of N-vinylpyrollidone, hydroxyethyl cellulose, methyl cellulose, carboxymethyl cellulose, dextran, polyethyleneglycol (PEG), PEG/PPG block copolymers, homo- and copolymers of acrylic and methacrylic acid, polyurethanes, polyvinyl alcohol, polyvinylethers, maleic anhydride based copolymers, polyesters, vinylamines, polyethyleneimines, polyethyleneoxides, poly (carboxylic acids), polyamides, polyanhydrides, polyphosphazenes, and mixtures thereof.

In certain embodiments, buffers of interest include a biological buffer, including but not limited to N-(2-acetamido)-aminoethanesulfonic acid (ACES), acetate, N-(2-acetamido)-iminodiacetic acid (ADA), 2-aminoethanesulfonic acid (AES), ammonia, 2-amino-2-methyl-1-propanol (AMP), 2-amino-2-methyl-1,3-propanediol (AMPD), N-(1,1-dimethyl-2-hydroxyethyl)-3-amino-2-hydroxypropanesulfonic acid (AMPSO), N,N-bis-(2-hydroxyethyl)-2-aminoethanesulfonic acid (BES), bicarbonate, N,N'-bis-(2-hydroxyethyl)-glycine, [Bis-(2-hydroxyethyl)-imino]-tris-(hydroxymethylmethane) (BIS-Tris), 1,3-Bis[tris (hydroxymethyl)-methylamino]propane (BIS-Tris-propane), boric acid, dimethylarsinic acid, bovine serum albumin (BSA) 3-(Cyclohexylamino)-propanesulfonic acid (CAPS), 3-(cyclohexylamino)-2-hydroxy-1-propanesulfonic acid (CAPSO), carbonate, cyclohexylaminoethanesulfonic acid (CHES), citrate, 3-[N-Bis(hydroxyethyl)amino]-2-hydroxypropanesulfonic acid (DIPSO), formate, glycine, glycylglycine, N-(2-Hydroxyethyl)-piperazine-N'-ethanesulfonic acid (HEPES), N-(2-Hydroxyethyl)-piperazine-N'-3-propanesulfonic acid (HEPPS, EPPS), N-(2-Hydroxyethyl)-piperazine-N'-2-hydroxypropanesulfonic acid (HEPPSO), imidazole, malate, maleate, 2-(N-Morpholino)-ethanesulfonic acid (MES), 3-(N-Morpholino)-propanesulfonic acid (MOPS), 3-(N-Morpholino)-2-hydroxypropanesulfonic acid (MOPSO), phosphate, piperazine-N,N'-bis(2-ethanesulfonic acid) (PIPES), piperazine-N,N'-bis(2-hydroxypropanesulfonic acid) (POPSO), pyridine, polyvinylpyrrolidone (PVP), succinate, 3-{[Tris(hydroxymethyl)-methyl]-amino}-propanesulfonic acid (TAPS), 3-[N-Tris(hydroxymethyl)-methylamino]-2-hydroxypropanesulfonic acid (TAPSO), 2-Aminoethanesulfonic acid, AES (Taurine), trehalose, triethanolamine (TEA), 2-[Tris(hydroxymethyl)-methylamino]-ethanesulfonic acid (TES), N-[Tris(hydroxymethyl)-methyl]-glycine (tricine), Tris(hydroxymethyl)-aminomethane (Tris), glyceraldehydes, mannose, glucosamine, mannoheptulose, sorbose-6-phophate, trehalose-6-phosphate, maleimide, iodoacetates, sodium citrate, sodium acetate, sodium phosphate, sodium tartrate, sodium succinate, sodium maleate, magnesium acetate, magnesium citrate, magnesium phosphate, ammonium acetate, ammonium citrate, ammonium phosphate, among other buffers.

The amount of each buffer component present in the porous matrix may vary, depending on the type and size of sample and the type of porous matrix employed (inorganic frit, porous organic polymer, as described above) and may range from 0.001% to 99% by weight, such as from 0.005% to 95% by weight, such as from 0.01% to 90% by weight, such as from 0.05% to 85% by weight, such as from 0.1% to 80% by weight, such as from 0.5% to 75% by weight, such as from 1% to 70% by weight, such as from 2% to 65% by weight, such as from 3% to 60% by weight, such as from 4% to 55% by weight and including from 5% to 50% by weight. For instance, the dry weight of buffer present in the porous matrix may range from 0.001 μg to 2000 μg, such as from 0.005 μg to 1900 μg, such as from 0.01 μg to 1800 μg, such as from 0.05 μg to 1700 μg, such as from 0.1 ng to 1500 μg, such as from 0.5 μg to 1000 μg and including a dry weight of buffer of from 1 μg to 500 μg.

In some embodiments, the total weight of buffer present in the porous matrix depends on the void volume (i.e., volume within the pores) of the porous matrix and ranges from 0.001 g to 5 g of buffer per mL of void volume in the porous matrix, such as from 0.005 g to 4.5 g, such as from 0.01 g to 4 g, such as from 0.05 g to 3.5 g, such as from 0.1 g to 3 g, such as from 0.5 g to 2.5 g and including from 1 g to 2 g of buffer per mL of void volume in the porous matrix.

In one example, buffer present in the porous matrix includes bovine serum albumin (BSA). Where buffer present in the porous matrix include BSA, the amount of BSA varies, ranging from 1% to 50% by weight, such as from 2% to 45% by weight, such as from 3% to 40% by weight, such as from 4% and 35% by weight and including from 5% and 25% by weight. For instance, the dry weight of BSA in the buffer may range from 0.001 μg to 2000 μg, such as from 0.005 μg to 1900 μg, such as from 0.01 μg to 1800 μg, such as from 0.05 μg to 1700 μg, such as from 0.1 ng to 1500 μg, such as from 0.5 μg to 1000 μg and including a dry weight of BSA of from 1 μg to 500 μg.

In another example, buffer present in the porous matrix includes polyvinylpyrrolidone (PVP). Where buffer present in the porous matrix include PVP, the amount of PVP varies, ranging from 0.01% to 10% by weight, such as from 0.05% to 9% by weight, such as from 0.1% to 8% by weight, such as from 0.5% and 7% by weight and including from 1% and 5% by weight. For instance, the dry weight of PVP in the buffer may range from 0.001 μg to 2000 μg, such as from 0.005 μg to 1900 μg, such as from 0.01 μg to 1800 μg, such as from 0.05 μg to 1700 μg, such as from 0.1 ng to 1500 μg, such as from 0.5 μg to 1000 μg and including a dry weight of PVP of from 1 μg to 500 μg.

In yet another example, buffer present in the porous matrix includes trehalose. Where buffer present in the porous matrix include trehalose, the amount of trehalose varies, ranging from 0.001% to 99% by weight, such as from 0.005% to 95% by weight, such as from 0.01% to 90% by weight, such as from 0.05% to 85% by weight, such as from 0.1% to 80% by weight, such as from 0.5% to 75% by weight, such as from 1% to 70% by weight, such as from 2% to 65% by weight, such as from 3% to 60% by weight, such as from 4% to 55% by weight and including from 5% to 50% by weight. For instance, the dry weight of trehalose in the buffer may range from 0.001 μg to 2000 μg, such as from 0.005 μg to 1900 μg, such as from 0.01 μg to 1800 μg, such as from 0.05 μg to 1700 μg, such as from 0.1 ng to 1500 μg, such as from 0.5 μg to 1000 μg and including a dry weight of trehalose of from 1 μg to 500 μg.

In certain embodiments, buffer present in the porous matrix includes BSA, trehalose and polyvinylpyrrolidone. For example, the buffer may include BSA, trehalose and polyvinylpyrrolidone in a weight ratio of BSA:trehalose: PVP which ranges from 1:1:1 and 25:100:1 In certain instances, the weight ratio of BSA:trehalose:PVP is 21:90:1.

In some embodiments, buffers may further include one or more complexing agents. A "complexing agent" is used to in its conventional sense to refer to an agent that aids in the mixing of the sample with the assay reagent and may also serve to tie up ions (e.g., iron or other ions) and preventing formation of precipitates during mixing. A complexing agent may be an agent that is capable of complexing with a metal ion. In some instances, the complexing agent is a chelating agent, such as ethylenediamine tetraacetatic acid (EDTA), diethylene triamine pentacetic acid (DTPA), nitrolotriacetic acid (NTA), ethylenediaminediacetate (EDDA), ethylenediaminedi(o-hydroxyphenylacetic) acid (EDDHA), hydroxyethylethylene-diaminetriacetic acid (HEDTA), cyclohexane diamine tetraacetic acid (CDTA) ethyleneglycol-bis-(beta-aminoethyl ether) N,N,N',N'-tetraacetic acid (EGTA), 2,3-dimercaptopropanel-1-sulfonic acid (DMPS), and 2,3-dimercaptosuccinic acid (DMSA) and the like. Naturally occurring chelating agents may also be employed. By naturally occurring chelating agent is meant that the chelating agent is a chelating agent that occurs in nature, i.e., not an agent that has been first synthesized by human intervention. The naturally occurring chelating agent may be a low molecular weight chelating agent, where by low molecular weight chelating agent is meant that the molecular weight of the chelating agent does not exceed about 200 daltons. In certain embodiments, the molecular weight of the chelating agent is greater than about 100 daltons. In some embodiments, assay reagents of interest include ethylenediamine tetraacetatic acid (EDTA). Where a chelating agent is present in the porous matrix, the amount of chelating agent may range from 0.001% to 10% by weight, such as from 0.005% to 9.5% by weight, such as from 0.01% to 9% by weight, such as from 0.05% to 8.5% by weight, such as from 0.1% to 8% by weight, such as from 0.5% to 7.5% by weight and including from 1% to 7% by weight. For instance, the dry weight of the chelating agent in the assay reagent may range from 0.001 μg to 2000 μg, such as from 0.005 μg to 1900 μg, such as from 0.01 μg to 1800 μg, such as from 0.05 μg to 1700 μg, such as from 0.1 ng to 1500 μg, such as from 0.5 μg to 1000 μg and including a dry weight of chelating agent of from 1 μg to 500 μg.

All or part of the porous matrix may contain the assay reagent and buffer components. For example, 5% or more of the porous matrix may contain assay reagent and buffer components, such as 10% or more, such as 25% or more, such as 50% or more, such as 75% or more, such as 90% or more, such as 95% or more and including 99% or more. In certain embodiments, the entire porous matrix contains assay reagent and buffer components. The assay reagent and buffer components may be homogeneously distributed throughout the porous matrix or may be positioned at discrete locations within the porous matrix, or some combination thereof. For instance, in one example, the assay reagent and buffer components are homogeneously distributed throughout the porous matrix. In another example, the assay reagent and buffer components are positioned at discrete locations in the porous matrix, such as in discrete increments of every 0.1 mm or more, such 0.5 mm or more, such as 1 mm or more and including positioning the porous matrix at every 2 mm or more of the porous matrix. In yet another example, the assay reagent and buffer components may be homogeneously distributed throughout a first half of the porous matrix and in discrete increments along a second half of the porous matrix. In certain embodiments, the assay reagent and buffer components are positioned in the porous matrix as a gradient, where the amount of assay reagent and buffer components increases from a proximal end (e.g., closer to sample application site) to the distal end (e.g., closer to flow channel). In one instance, the amount of assay reagent increases linearly along the sample flow path through the porous matrix. In another instance, the amount of assay reagent and buffer components increases exponentially along the sample flow path through the porous matrix.

The assay reagents and buffer components may be present in the porous component in any suitable physical state, such as a liquid, dry solid or may be lyophilized. In some embodiments, the assay reagents and buffer components are present as a dry solid. In other embodiments, the assay reagents and buffer components are lyophilized. All or part of the assay reagents and buffer components may be in the same physical state. For example 5% or more of the assay reagents and buffer components may be present in the porous matrix as a dry solid, such as 10% or more, such as 25% or more, such as 50% or more, such as 75% or more, such as 90% or more and including 95% or more of the assay reagents and buffer components. In some embodiments, 5% or more of the assay reagents and buffer components are lyophilized, such as 10% or more, such as 25% or more, such as 50% or more, such as 75% or more, such as 90% or more and including where 95% or more of the assay reagents and buffer components are lyophilized.

In embodiments of the present disclosure, a flow channel is positioned adjacent to the porous component and in fluid communication with the sample mixed with assay reagent and buffer components in the porous matrix. As discussed in greater detail below, the sample may be passed through and mixed with the assay reagent in the porous matrix by a force (e.g., centrifugal force, electrostatic force, capillary action) and into the flow channel. In some embodiments, the flow channel is an elongated channel enclosed by one or more walls. Depending on the size of the sample, the flow channel may vary. In some embodiments, the flow channel is linear. In other embodiments, the flow channel is non-linear. For example, the flow channel may be curvilinear, circular, winding, twisted or have a helical configuration.

The length of the flow channel may vary, ranging from 10 mm to 1000 mm, such as from 15 mm to 950 mm, such as from 20 mm to 900 mm, such as from 20 mm to 850 mm, such as from 25 mm to 800 mm, such as from 30 mm to 750 mm, such as from 35 mm to 700 mm, such as from 40 mm to 650 mm, such as from 45 mm to 600 mm, such as from 50 mm to 550 mm and including from 100 mm to 500 mm.

In embodiments, the cross-sectional shape of the flow channel may vary, where examples of cross-sectional shapes include, but are not limited to rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. In embodiments, the cross-sectional dimensions of the flow channel may vary, ranging from 0.01 mm to 25 mm, such as from 0.05 mm to 22.5 mm, such as from 0.1 mm to 20 mm, such as from 0.5 mm to 17.5 mm, such as from 1 mm to 15 mm, such as from 2 mm to 12.5 mm, such as from 3 mm to 10 mm and including from 5 mm to 10 mm. For example, where the flow channel is cylindrical, the diameter of the flow channel may range from 0.01 mm to 25 mm, such as from 0.05 mm to 22.5 mm, such as from 0.1 mm to 20 mm, such as from 0.5 mm to 15 mm, such as from 1 mm to 10 mm and including from 3 mm to 5 mm.

The ratio of length to cross-sectional height may vary, ranging from 2 to 5000, such as from 3 to 2500, such as from 4 to 2000, such as from 5 to 1500, such as from 10 to 1000, such as from 15 to 750 and including from 25 to 500. In some instances, the ratio of length to cross-sectional height is 10. In other instances, the ratio of length to cross-sectional height is 15. In yet other instances, the ratio of length to cross-sectional height is 25.

In some embodiments, the flow channel is configured to have a cross-sectional height which is substantially equivalent to the dimensions of the target analyte. By "substantially equivalent" to the dimensions of the target analyte is meant that one or more of the height or width of the flow channel differs from the size of the target analyte by 5% or less, such as 4% or less, such as 3% or less, such as 2% or less, such as 1% or less, such as 0.5% or less, such as 0.1% or less and including 0.01% or less. In these embodiments, the cross-sectional dimensions of the flow channel are substantially the same as the size of the target analyte and the target analytes are configured to flow through the flow channel one analyte at a time. In certain instances, the target analyte are cells, such as white blood cells or red blood cells. In some embodiments, the flow channel is configured to have a cross-sectional height which substantially equivalent to the diameter of a red blood cell. In other embodiments, the flow channel is configured to have a cross-sectional height which is substantially equivalent to the diameter of a white blood cell.

In embodiments of the present disclosure, the flow channel is a structure configured to receive and retain a sample having a volume ranging from 5 μL to 5000 μL, such as from 10 μL to 4000 μL, such as from 15 μL to 3000 μL, such as from 20 μL to 2000 μL, such as from 25 μL to 1000 μL, such as from 30 μL to 500 μL, such as from 40 μL to 400 μL, such as from 50 μL to 300 μL and including from 75 μL to 250 μL.

In some embodiments, the flow channel is a capillary channel and is configured to move a liquid sample through the flow channel by a capillary action. The term "capillary action" is used herein in its conventional sense to refer to the movement of a liquid by intermolecular forces between the liquid (i.e., cohesion) and the surrounding walls (i.e., adhesion) of a narrow channel without the assistance of (and sometimes in opposition to) gravity. In these embodiments, the cross-sectional width of the flow channel is sufficient to provide for capillary action of the sample in the flow channel and may have a width ranging from 0.1 mm to 20 mm, such as from 0.5 mm to 15 mm, such as from 1 mm to 10 mm and including from 3 mm to 5 mm.

In some embodiments, the flow channel includes one or more optically transmissive walls. By "optically transmissive" is meant that the walls of the flow channel permit the propagation of one or more wavelengths of light therethrough. In some embodiments, the walls of the flow channel are optically transmissive to one or more of ultraviolet light, visible light and near-infrared light. In one example, the flow channel is optically transmissive to ultraviolet light. In another example, the flow channel is optically transmissive to visible light. In yet another example, the flow channel is optically transmissive to near-infrared light. In still another example, the flow channel is transmissive to ultraviolet light and visible light. In still another example, the flow channel is transmissive to visible light and near-infrared light. In still another example, the flow channel is transmissive to ultraviolet light, visible light and near-infrared light. Depending on the desired transmissive properties of the flow channel walls, the optically transmissive wall may be any suitable material, such as quartz, glass, or polymeric, including but not limited to optically transmissive polymers such as acrylics, acrylics/styrenes, cycloolefin polymers, polycarbonates, polyesters and polystyrenes, among other optically transmissive polymers.

In embodiments of the present disclosure, the sample application site of the microfluidic device is a structure configured to receive a sample having a volume ranging from 5 μL to 1000 μL, such as from 10 μL to 900 μL, such as from 15 μL to 800 μL, such as from 20 μL to 700 μL, such as from 25 μL to 600 μL, such as from 30 μL to 500 μL, such as from 40 μL to 400 μL, such as from 50 μL to 300 μL and including from 75 μL to 250 μL. The sample application site may be any convenient shape, so long as it provides for fluid access, either directly or through an intervening component that provides for fluidic communication, to the flow channel. In some embodiments, the sample application site is planar. In other embodiments, the sample application site is concave, such as in the shape of an inverted cone terminating at the sample inlet orifice. Depending on the amount of sample applied and the shape of the sample application site, the sample application site may have a surface area ranging from 0.01 $mm^2$ to 1000 $mm^2$, such as from 0.05 $mm^2$ to 900 $mm^2$, such as from 0.1 $mm^2$ to 800 $mm^2$, such as from 0.5 $mm^2$ to 700 $mm^2$, such as from 1 $mm^2$ to 600 $mm^2$, such as from 2 $mm^2$ to 500 $mm^2$ and including from 5 $mm^2$ to 250 $mm^2$.

The inlet of the microfluidic device is in fluidic communication with sample application site and the flow channel and may be any suitable shape, where cross-sectional shapes of inlets of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. The dimensions of the nozzle orifice may vary, in some embodiments ranging from 0.01 mm to 100 mm, such as from 0.05 mm to 90 mm, such as from 0.1 mm to 80 mm, such as from 0.5 mm to 70 mm, such as from 1 mm to 60 mm, such as from 2 mm to 50 mm, such as from 3 mm to 40 mm, such as from 4 mm to 30 mm and including from 5 mm to 25 mm. In some embodiments, the inlet is a circular orifice and the diameter of the inlet ranges from 0.01 mm to 100 mm, such as from 0.05 mm to 90 mm, such as from 0.1 mm to 80 mm, such as from 0.5 mm to 70 mm, such as from 1 mm to 60 mm, such as from 2 mm to 50 mm, such as from 3 mm to 40 mm, such as from 4 mm to 30 mm and including from 5 mm to 25 mm. Accordingly, depending on the shape of the inlet, sample inlet orifice may have an opening which varies, ranging from 0.01 $mm^2$ to 250 $mm^2$, such as from 0.05 $mm^2$ to 200 $mm^2$, such as from 0.1 $mm^2$ to 150 $mm^2$, such as from 0.5 $mm^2$ to 100 $mm^2$, such as from 1 $mm^2$ to 75 $mm^2$, such as from 2 $mm^2$ to 50 $mm^2$ and including from 5 $mm^2$ to 25 $mm^2$.

In some embodiments, the subject microfluidic devices include a venting channel. Venting channels of interest may have a variety of different configurations and is configured to couple in fluid communication a vent outlet (e.g., positioned adjacent to the sample application site) with the distal end of the flow channel (i.e., furthest from the sample application site). The venting channel may be an elongated structure, similar to those described above for the flow channel, including a configuration having a length that is longer than its width. While the ratio of length to width may vary, in some instances the ratio of length to width ranges from 5 to 2000 such as 10 to 200 and include 50 to 60. In some instances, the length of the venting channel ranges from 5 to 200, such as 10 to 100 and including 50 to 75 mm. In some instances, venting channels of interest have a micrometer sized longed cross-sectional dimension, e.g., a longest cross-sectional dimension (e.g., diameter in the case of the tubular channel) ranging from 0.1 to 10, such as 0.5 to 5 and including 1 to 2 mm. In some instances, the width of the venting channel ranges from 0.1 to 10, such as 0.5 to 5 and including 1 to 2 mm. In some instances the height of the channel ranges from 0.5 to 5, such as 0.2 to 2 and including 0.5 to 1 mm. The cross-sectional shape of the venting channels may vary, in some instances, cross-sectional shapes of the venting channels of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. In embodiments, the cross-sectional dimensions of the venting channel may vary, ranging from 0.01 mm to 25 mm, such as from 0.05 mm to 22.5 mm, such as from 0.1 mm to 20 mm, such as from 0.5 mm to 17.5 mm, such as from 1 mm to 15 mm, such as from 2 mm to 12.5 mm, such as from 3 mm to 10 mm and including from 5 mm to 10 mm. For example, where the venting channel is cylindrical, the diameter of the venting channel may range from 0.01 mm to 25 mm, such as from 0.05 mm to 22.5 mm, such as from 0.1 mm to 20 mm, such as from 0.5 mm to 15 mm, such as from 1 mm to 10 mm and including from 3 mm to 5 mm.

Where the subject microfluidic devices include a venting channel, the flow channel may be separated from the venting channel by a hydrophobic region. By hydrophobic region is meant a region or domain that is resistant to being wetted by water, e.g., it repels aqueous media. The hydrophobic region may be one that has a surface energy that is lower than the surface energy of the surfaces of the capillary channel. The magnitude of difference in surface energies may vary, ranging in some instances from 5 to 500, such as 10 to 30 dynes/cm. The surface energy of the hydrophobic region may also vary, ranging in some instances from 20 to 60, such as 30 to 45 dynes/cm, e.g., as measured using the protocol described in ASTM Std. D2578. The dimensions of the hydrophobic region are configured to at least partially if not complete impede liquid flow of sample past the hydrophobic region. The dimensions of the hydrophobic region may vary, in some instances having a surface area ranging from 0.01 $mm^2$ to 100 $mm^2$, such as from 0.05 $mm^2$ to 90 $mm^2$, such as from 0.1 $mm^2$ to 80 $mm^2$, such as from 0.5 $mm^2$ to 75 $mm^2$ and including from 1 $mm^2$ to 50 $mm^2$.

With reference to FIG. 1, a microfluidic device for assaying a sample according to certain embodiments, such as with an imaging apparatus as described in Goldberg, U.S. patent publication 2008/0212069 is shown. FIG. 1 depicts an example of a microfluidic device having a sample application site (1), porous component (porous element 2), and a flow channel (e.g., capillary channel 3). As shown in FIG. 1, the microfluidic device also includes a hydrophobic junction (4) and a venting channel (5). To visualize sample in the flow channel, this example depicts a flow channel having an optically transmissive wall (6). The sample application site is configured to receive a fluid sample, such as a biological fluid (e.g., blood, saliva, serum, semen, plasma, or the like). In some embodiments, the sample is a blood sample. As discussed above, the sample application site is in fluid communication with the porous component in a manner that directs the sample of a sample through the porous component. The porous component may be disposed in a chamber or channel in such a manner that the sample is directed through the porous element. The porous element may be flush with the microfluidic device walls disposed either in a fitted chamber in the device or along a capillary or other channel. In some embodiments, the sample application site and the porous component are configured in a manner that provides for the flow of a sample from the sample application site through the porous matrix of the porous component and capillary channel by a capillary force, but other means of sample motion are possible. Centrifugal force, electrostatic force or any other force may be used alone or in conjunction with capillary force to transmit sample through the porous element. The sample application site may support the application of a sample dispensed by any means such as from a pipette or directly from an organism such via a finger-stick blood sample from a human.

In some embodiments, the porous component includes a porous frit made up of a plurality of microchannels that serve as a matrix for an assay mixture. As described above, the microchannels may form a void volume in the frit that is between 40 and 60% of the total frit volume. In some embodiments, the frit may occupy a volume of about 10 µl and the total void volume may between 4 and 6 µl. In some embodiments, the pores are as narrow as possible to provide for sufficient surface area for suspension of dried reagent and tortuous path for mixing, without filtering cells or other objects up to 15-20 microns. The assay mixture may be dried or otherwise preserved within the void volume of the frit and may comprise buffer components and one or more reagents such as a detectable label that binds to one or more targets or analytes in the sample. The buffer components may provide for a uniform dissolution rate of the reagent into the sample over a defined period of time. The buffer components may comprise any combination of a protein, sugar and/or a chemical binder. The protein component may be an albumin such as bovine serum albumin (BSA). The sugar may be any sugar such as a mono, di, or polysaccharide. For example, sucrose, mannitol, trehalose (such as $D^+$ trehalose) may stabilize biomolecules or other reagents in the porous frit and afford protection to reagents such as biomolecules. In the development of lyophilized or preserved reagents, proteins or sugars (saccharides and polyols) may be added to the formulation in order to improve the stability and provide for uniform dissolution of reagents or other biomolecules and additionally and prolong the shelf life of reagents in the device.

Low molecular weight dextran, cyclodextrin, polyethylene glycol, polyethylene glycol ester polyvinylpyrollidone (PVP) or other hydrophilic polymers selected from the group consisting of hyaluronic acid, polyvinylpyrollidone (PVP), copolymers of N-vinylpyrollidone, hydroxyethyl cellulose, methyl cellulose, carboxymethyl cellulose, dextran, Polyethyleneglycol (PEG), PEG/PPG block copolymers, homo- and copolymers of acrylic and methacrylic acid, polyurethanes, polyvinyl alcohol, polyvinylethers, maleic anhydride based copolymers, polyesters, vinylamines, polyethyleneimines, polyethyleneoxides, poly(carboxylic acids), polyamides, polyanhydrides, polyphosphazenes, and mixtures thereof may be used to stabilize the reagent and aid in the continuous dissolution of the reagent in the sample.

The buffer components may be assembled in the appropriate ratio and concentration to provide for the continuous dissolution of a reagent into a sample. The total amount of buffer components may depend on the void volume of the porous frit. In some embodiments the combined weight of the buffer components (e.g., BSA, trehalose, and PVP) may be between 0.01 and 2 grams per μl of frit void volume, such as 0.1 gram/μl void volume. In some embodiments the buffer components of this invention may contain a weight ratio of BSA:Trehalose:PVP that is on the order of 21:90:1. The weight ratio of the buffer components may vary as much as 5, 10 or 20% provided that the property of uniform dissolution of the reagent in a liquid sample over a pre-determined period of time is maintained. The pre-determined period of time may be on the order of seconds or minutes such as between 5 seconds and 5 minutes or between 20 seconds and 3 minutes, or between 1 and 2 minutes during which a uniform dissolution of reagent into the sample is maintained. This provides for improved uniformity of the distribution of unbound reagent in the sample through the capillary channel and sample interrogation. The concentration of unreacted reagent typically may deviate by less than 1%, 5%, 10%, 20% or 50% over the course of the capillary channel. In some embodiments the buffer components may contain components such as ethylenediaminetetraacetic acid (EDTA) or 2-(N-morpholino) ethanesulfonic acid (MES) or the like or any other material useful for maintaining the stability of the sample or reagents during the course of the assay. The assay mixture may comprise enzymes, substrates, catalysts, or any combination thereof for reaction with the sample (e.g., horseradish peroxidase, pyruvate oxidase, oxaloacetate decarboxylase, creatinine amidohydrolase, creatine amidinohydrolase, sarcosine oxidase, malate dehydrogenase, lactate dehydrogenase, FAD, TPP, P-5-P, NADH, amplex red). Other components of the assay mixture may be used to regulate the pH, dissolution rate, or stability of the sample and/or the assay mixture (e.g., hydroxypropyl methyl cellulose, hydroxypropyl cellulose). As the sample flows through the porous element, the microchannels provide for the mixing of the sample and the reagent while the uniform dissolution rate of the reagent provides for the substantially uniform distribution of unreacted reagent as it flows out of the porous matrix and into the flow channel.

As discussed above, the assay reagents may include any material capable of reacting with or binding to an analyte in a biological sample as desired. In some embodiments, the reagent is an antibody or antibody fragment that binds to components in the sample, such a specific cell surface target in the sample. There may be one or more distinct reagents in the assay mixture. In some embodiments the antibody or antibody fragments may specifically bind to cellular targets such as CD14, CD4, CD45RA, CD3, or any combination thereof. The antibody or antibody fragments may be conjugated to a dye or other detectable label such as a fluorescent dye or magnetic particle. In some embodiments the detectable label is a dye selected from the group comprising rhodamine, coumarin, cyanine, xanthene, polymethine, pyrene, dipyrromethene borondifluoride, napthalimide, phycobiliprotein, peridinium chlorophyll proteins, conjugates thereof, and combinations thereof. In some embodiments the dye may be phycoerythrin (PE), phycoerythrin cyanine 5, (PE-cy5) or allophycocyanin (APC). The detectable label may be magnetic, phosphorescent, fluorescent or optically active in any way.

As depicted in FIG. 1, microfluidic devices of interest according to certain embodiments include a capillary chamber having a flat geometry with large width and length dimensions and a height either (a) substantially equivalent to the depth of field of an objective lens of a detector, or (b) just slightly larger than the cells to be analyzed in a sample. The sample may be optically interrogated through one or more transmissive walls in the microfluidic device. The uniform distribution of unreacted reagent in the sample provides for improved observations of background signal along the length of the transmissive wall. This beneficially provides for easier detection of bound reagent as concentrations of detectable signal above background are observed.

Figure 2:
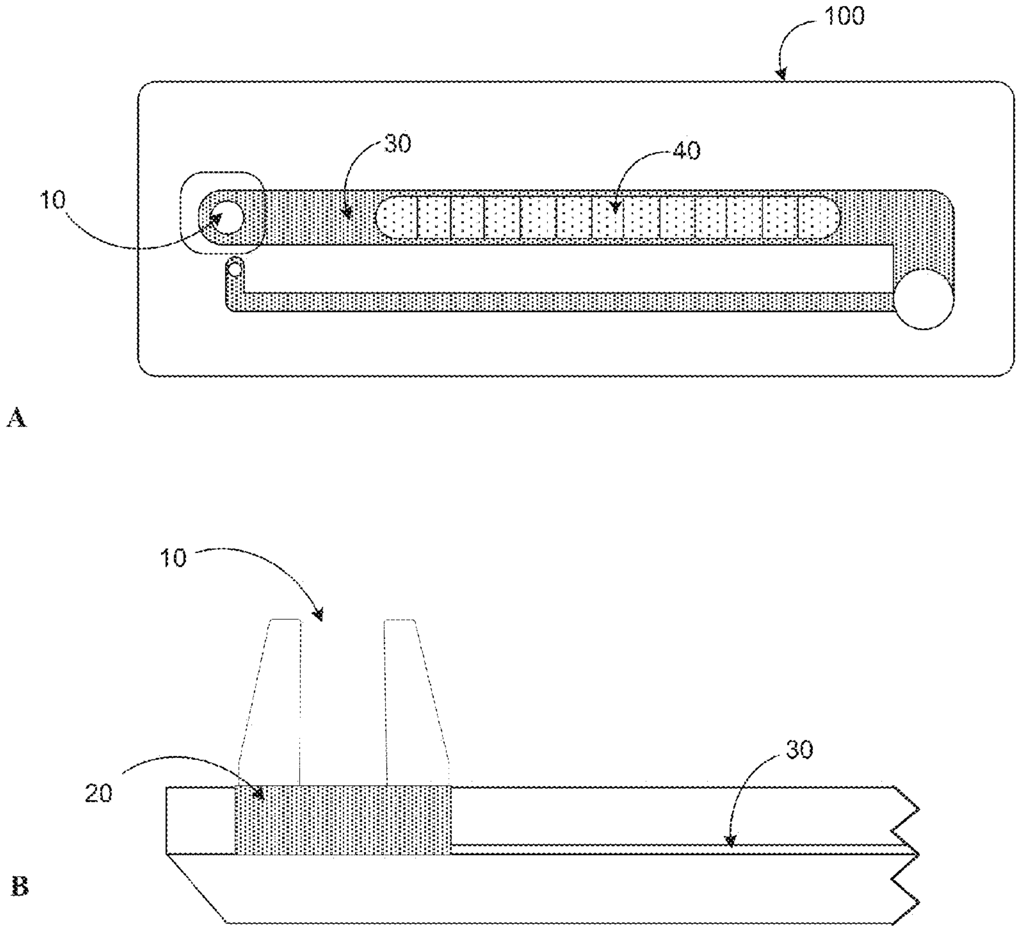
FIG. 2 panel A depicts schematic showing a top view of a microfluidic device according to certain embodiments.

Another example of a microfluidic device (100) is illustrated in greater detail in FIGS. 2A and 2B and include a sample application site 10 in fluidic communication with a porous component 20 and flow channel 30. In this embodiment, the flow channel includes optically transmissive wall 40. The frit portion of the porous component may be prepared from any suitable material such as plastic (e.g., polyethylene, polypropylene, polytetrafluoroethylene, polyvinylidene fluoride, ethyl vinyl acetate, polycarbonate, polycarbonate alloys, polyurethane, polyethersulfone or any combination thereof), as discussed above. In some embodiments, the porous matrix is high density polyethylene. The porous matrix may be a solid of any size or shape that fills a region between the flow channel and the application site. The porous element may be disposed in a distinct chamber or merely occupying a region of the capillary channel. The porous frit external dimensions are designed in concert with overall device so the porous frit fits snugly into the overall device and essentially no sample goes around the porous frit. In some embodiments the porous frit is integrated as part of the flow channel. The porous frit may be a solid material comprised of a series of microchannels and having a void volume of between 25 and 75%, such as 40-60% or 45-55%. The microchannels may provide for the mixing of the assay mixture and a sample via a plurality of tortuous paths. In some embodiments the average through-pore diameter of the microchannels may be between 5 and 200 microns, such as between 30 and 60 microns; and the average void volume may be 40-60% of the total frit volume. The average diameter and tortuous path of the microchannels may beneficially provide for mixing of the sample and reagent, while allowing the sample to flow through the porous element substantially unfiltered. The device may utilize any force such as gravity or centrifugal force in addition to capillary force to provide movement of the sample through the flow channel.

Where the subject microfluidic devices employ capillary action, microfluidic devices do so because the flow surfaces are hydrophilic, and wetting of the surfaces is energetically favorable. Such devices require the incoming sample to displace the air resident in the device. It is desirable for both the applied sample as well as the vented air to be contained within the cartridge in order to protect users from potentially bio-hazardous material. In some embodiments of the present disclosure any combination of the following features may be utilized in the device. For example the capillary channel or the sample application site may include a mixing chamber where preserved reagents may be located separate from the capillary channel. The dimensions of the capillary channel may impact the imaging and flow of sample in the device. In some embodiments the channel may be between 2 and 10 mm wide such as between 3 and 5 mm or between 3 and 4 mm wide. In some embodiments the capillary channel may be between 1 and 1000 microns deep, such as between 20 and 60 microns deep or between 40 and 60 microns deep. Depths less than 60 microns deep may beneficially provide for imaging white blood cells in a whole blood sample by minimizing the obscuring effects of red blood cells. The capillary channel may be any length that provides for capillary flow along a channel. In some embodiments the capillary channel may be between 10 and 100 mm long.

As discussed above, the device is suitable for assays to detect analytes in a sample comprising a biological fluid, such as urine, saliva, plasma, blood, in particular, whole blood. Specific components of the sample may be distinguishably labeled using fluorescent dyes that are distinguishable from each other. In this manner, the components may be distinguished by their fluorescent emissions.

Methods for Assaying a Sample

Aspects of the disclosure also include methods for assaying a sample. As discussed above, the term "assaying" is used herein in its conventional sense to refer to qualitatively assessing or quantitatively measuring the presence or amount of a target analyte species. A variety of different samples may be assayed by the subject methods. In some instances, the sample is a biological sample. The term "biological sample" is used in its conventional sense to include a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may include any type of organismic material, including both healthy and diseased components (e.g., cancerous, malignant, necrotic, etc.). In certain embodiments, the biological sample is a liquid sample, such as whole blood or derivative thereof, plasma, tears, sweat, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. Biological samples of interest may be obtained from human subjects of both genders and at any stage of development (i.e., neonates, infant, juvenile, adolescent, adult), where in certain embodiments the human subject is a juvenile, adolescent or adult. While the present disclosure may be applied to samples from a human subject, it is to be understood that the subject methods may be employed to assay samples from other non-human animal subjects such as, but not limited to, birds, mice, rats, dogs, cats, livestock and horses.

In embodiments, the amount of sample assayed in the subject methods may vary, for example, ranging from 0.01 μL to 1000 μL, such as from 0.05 μL to 900 μL, such as from 0.1 μL to 800 μL, such as from 0.5 μL to 700 μL, such as from 1 μL to 600 μL, such as from 2.5 μL to 500 μL, such as from 5 μL to 400 μL, such as from 7.5 μL to 300 μL and including from 10 μL to 200 μL of sample.

The sample may be applied to the sample application site using any convenient protocol, e.g., via dropper, pipette, syringe and the like. The sample may be applied in conjunction or incorporated into a quantity of a suitable liquid, e.g., buffer, to provide for adequate fluid flow. Any suitable liquid may be employed, including but not limited to buffers, cell culture media (e.g., DMEM), etc. Buffers include, but are not limited to: tris, tricine, MOPS, HEPES, PIPES, MES, PBS, TBS, and the like. Where desired, detergents may be present in the liquid, e.g., NP-40, TWEEN™ or TritonX100 detergents.

In some embodiments, the biological sample is preloaded into a microfluidic device (as described above) and stored for a predetermined period of time before measuring the biological sample in the flow channel. For example, the biological sample may be preloaded into the microfluidic device, as described in greater detail below, for a period of time before the biological sample in the flow channel is measured according to the subject methods. The amount of time the biological sample is stored following preloading may vary, such as 0.1 hours or more, such as 0.5 hours or more, such as 1 hour or more, such as 2 hours or more, such as 4 hours or more, such as 8 hours or more, such as 16 hours or more, such as 24 hours or more, such as 48 hours or more, such as 72 hours or more, such as 96 hours or more, such as 120 hours or more, such as 144 hours or more, such as 168 hours or more and including preloading the biological sample into the container 240 hours or more before assaying the biological sample or may range such as from 0.1 hours to 240 hours before assaying the biological sample, such as from 0.5 hours to 216 hours, such as from 1 hour to 192 hours and including from 5 hours to 168 hours before assaying the biological sample.

In certain embodiments, the biological sample is preloaded into the microfluidic device and sample in the flow channel is measured at a remote location (e.g., a laboratory for assaying in accordance with the subject methods). By "remote location" is meant a location other than the location at which the sample is contained and preloaded into the container. For example, a remote location could be another location (e.g., office, lab, etc.) in the same city, another location in a different city, another location in a different state, another location in a different country, etc., relative to the location of the processing device, e.g., as described in greater detail below. In some instances, two locations are remote from one another if they are separated from each other by a distance of 10 m or more, such as 50 m or more, including 100 m or more, e.g., 500 m or more, 1000 m or more, 10,000 m or more, etc.

In practicing methods according to certain embodiments, a sample is contacted with a sample application site of a microfluidic device (as described above), the sample passing from the sample application site through a porous component where the sample mixes with an assay reagent in a porous matrix and into a flow channel. As summarized above, passing the sample through the porous component mixes the sample with an assay reagent. In some embodiments, the sample passes through the porous matrix into the flow channel without loss of any of the sample components. The term "without loss" is meant that the network of interconnected pores of the porous matrix does not does not substantially restrict the passage of sample components through to the flow channel, such as where 99% or more of the sample passes through the porous matrix into the flow channel, such as 99.5% or more, such as 99.9% or more, such as 99.99% or more, such as 99.999% or more and including passage of 99.9999% or more of the sample through the porous matrix. In certain embodiments, all (i.e., 100%) of the sample passes through the porous matrix. In other words, 1% or less of sample components are restricted by the pores of the porous matrix, such as 0.9% or less, such as 0.8% or less, such as 0.7% or less, such as 0.5% or less, such as 0.1% or less, such as 0.05% or less, such as 0.01% or less, such as 0.001% or less and including where 0.0001% or less of the sample components are restricted by the pores of the porous matrix. Put another way, 1% or less of the sample remains in the porous matrix after passage of the sample into the flow channel, such as 0.9% or less, such as 0.8% or less, such as 0.7% or less, such as 0.5% or less, such as 0.1% or less, such as 0.05% or less, such as 0.01% or less, such as 0.001% or less and including 0.0001% or less of the sample remains in the porous matrix after passage of the sample into the flow channel.

In embodiments, passing the sample through the porous matrix provides for mixing the sample with an assay reagent in the porous matrix. In some embodiments, mixing the sample with the assay reagent includes coupling one or more components of the sample with an analyte-specific binding member. By "coupling" is meant that the sample component and analyte-specific binding member forms one or more physical or chemical bonds to each other, including but not limited to coupling by ionic, dipolar, hydrophobic, coordinative, covalent, van der Waals or hydrogen bonding interactions to couple the sample component with the analyte-specific binding member. In some instances, coupling the sample component to an analyte-specific binding member includes covalently bonding the sample component to the analyte-specific binding member. In certain instances, coupling the sample component to an analyte-specific binding member includes non-covalently bonding (e.g., through hydrogen bonding) the sample component to the analyte-specific binding member. For example coupling between the analyte-specific binding member and the target analyte may be characterized by a dissociation constant, such as dissociation constant of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less and including $10^{-16}$ M or less.

As discussed above, analyte-specific binding members may vary depending on the sample being assayed and the target analytes of interest and may include, but are not limited to antibody binding agents, proteins, peptides, haptens, nucleic acids, oligonucleotides. In some embodiments, the analyte-specific binding member is an enzyme. Examples of analyte-specific binding enzymes may be horseradish peroxidase, pyruvate oxidase, oxaloacetate decarboxylase, creatinine amidohydrolase, creatine amidinohydrolase, sarcosine oxidase, malate dehydrogenase, lactate dehydrogenase, FAD, TPP, P-5-P, NADH, amplex red and combinations thereof.

In certain embodiments, methods include passing the sample through the porous component to couple one or more components of the sample to an antibody binding agent. The antibody binding agent can be, for example, a polyclonal or monoclonal antibody or a fragment sufficient to bind to the analyte of interest. The antibody fragments can be in some instances monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. In certain embodiments, one or more components of the sample are coupled to an antibody or antibody fragment that binds specifically to a compound such as CD14, CD4, CD45RA and CD3 or a combination thereof.

In embodiments, the analyte-specific binding agent may be coupled to a detectable label, such as radioactive labels, labels detectable by spectroscopy techniques such as nuclear magnetic resonance as well as optically detectable labels. In some embodiments, mixing the sample with the assay reagent in the porous matrix includes coupling one or more components of the sample to an analyte-specific binding member conjugated to an optically detectable label. In certain instances, the optically detectable label is detectable by emission spectroscopy, such as by fluorescence spectroscopy. In these instances, the optically detectable label is a fluorophore such as 4-acetamido-4'-isothiocyanatostilbene-2,2'disulfonic acid; acridine and derivatives such as acridine, acridine orange, acridine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene or combinations thereof, among other fluorophores. In certain embodiments, the fluorophore is a fluorescent dye such as rhodamine, coumarin, cyanine, xanthene, polymethine, pyrene, dipyrromethene borondifluoride, napthalimide, phycobiliprotein, peridinium chlorophyll proteins, conjugates thereof or a combination thereof.

In practicing the subject methods, after the sample has mixed with the assay reagent in the porous matrix and is passed into the flow channel (e.g., by capillary action), the sample is illuminated in the flow channel with a source of light. Depending on the type of sample and target analytes being assayed, the sample may be illuminated in the flow channel immediately after the sample has passed through the porous matrix and into the flow channel. In other embodiments, the sample is illuminated following a predetermined period of time after the sample is contacted with the assay reagents in the porous matrix, such as a period of time ranging from 10 seconds to 1 hour, such as 30 seconds to 30 minutes, e.g., 30 seconds to 10 minutes, including 30 seconds to 1 minute. The sample may be illuminated with one or more sources of light. In some embodiments, the sample is illuminated with one or more broadband light sources. The term "broadband" is used herein in its conventional sense to refer to a light source which emits light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 400 nm to 700 nm. Another example of a suitable broadband light source includes a light source that emits light having wavelengths from 500 nm to 700 nm. Any convenient broadband light source protocol may be employed, such as a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, the sample is illuminated with one or more narrow band light sources emitting a particular wavelength or narrow range of wavelengths. The term "narrow band" is used herein in its conventional sense to refer to a light source which emits light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Any convenient narrow band light source protocol may be employed, such as a narrow wavelength LED, laser diode or a broadband light source coupled to one or more optical bandpass filters, diffraction gratings, monochromators or any combination thereof.

In certain embodiments, methods include irradiating the sample in the flow channel with one or more lasers. The type and number of lasers will vary depending on the sample as well as desired emitted light collected and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the methods include irradiating the sample in the flow channel with a dye laser, such as a stilbene, coumarin or rhodamine laser. In yet other instances, methods include irradiating the sample in the flow channel with a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, methods include irradiating the sample in the flow channel with a solid-state laser, such as a ruby laser, an Nd:YAG laser, NdCrYAG laser, Er:YAG laser, Nd:YLF laser, Nd:$YVO_4$ laser, Nd:$YCa_4O(BO_3)_3$ laser, Nd:YCOB laser, titanium sapphire laser, thulim YAG laser, ytterbium YAG laser, ytterbium$_2O_3$ laser or cerium doped lasers and combinations thereof.

Depending on the analyte being assayed as well as interferents present the biological sample, the biological sample may be illuminated using one or more light sources, such as two or more light sources, such as three or more light sources, such as four or more light sources, such as five or more light sources and including ten or more light sources. Any combination of light sources may be used, as desired. For example, where two lights sources are employed, a first light source may be a broadband white light source (e.g., broadband white light LED) and second light source may be a broadband near-infrared light source (e.g., broadband near-IR LED). In other instances, where two light sources are employed, a first light source may be a broadband white light source (e.g., broadband white light LED) and the second light source may be a narrow spectra light source (e.g., a narrow band visible light or near-IR LED). In yet other instances, the light source is an plurality of narrow band light sources each emitting specific wavelengths, such as an array of two or more LEDs, such as an array of three or more LEDs, such as an array of five or more LEDs, including an array of ten or more LEDs.

Where more than one light source is employed, the sample may be illuminated with the light sources simultaneously or sequentially, or a combination thereof. For example, where the sample is illuminated with two light sources, the subject methods may include simultaneously illuminating the sample with both light sources. In other embodiments, the sample may be sequentially illuminated by two light sources. Where the sample is sequentially illuminated with two or more light sources, the time each light source illuminates the same may independently be 0.001 seconds or more, such as 0.01 seconds or more, such as 0.1 seconds or more, such as 1 second or more, such as 5 seconds or more, such as 10 seconds or more, such as 30 seconds or more and including 60 seconds or more. In embodiments where the sample is sequentially illuminated by two or more light sources, the duration the sample is illuminated by each light source may be the same or different.

The time period between illumination by each light source may also vary, as desired, being separated independently by a delay of 1 second or more, such as 5 seconds or more, such as by 10 seconds or more, such as by 15 seconds or more, such as by 30 seconds or more and including by 60 seconds or more. In embodiments where the sample is sequentially illuminated by more than two (i.e., three or more) light sources, the delay between illumination by each light source may be the same or different.

Depending on the assay protocol, illumination of the sample may be continuous or in discrete intervals. For example, in some embodiments, the sample may be illuminated continuously throughout the entire time the sample is being assayed. Where the light includes two or more light sources, the sample may be continuously illuminated by all of the light sources simultaneously. In other instances, the sample is continuously illuminated with each light source sequentially. In other embodiments, the sample may be illuminated in regular intervals, such as illuminating the sample every 0.001 microseconds, every 0.01 microseconds, every 0.1 microseconds, every 1 microsecond, every 10 microseconds, every 100 microseconds and including every 1000 microseconds.

The sample may be illuminated with the light source one or more times at any given measurement period, such as 2 or more times, such as 3 or more times, including 5 or more times at each measurement period.

Depending on the light source and characteristics of the flow channel (e.g., flow channel width), the flow channel may be irradiated from a distance which varies such as 1 mm or more from the flow channel, such as 2 mm or more, such as 3 mm or more, such as 4 mm or more, such as 5 mm or more, such as 10 mm or more, such as 15 mm or more, such as 25 mm or more and including 50 mm or more from the flow channel. Also, the angle at which the flow channel is irradiate may also vary, ranging from 10° to 90°, such as from 15° to 85°, such as from 20° to 80°, such as from 25° to 75° and including from 30° to 60°. In certain embodiments, the flow channel is irradiated by the light source at a 90° angle with respect to the axis of the flow channel.

In certain embodiments, irradiating the flow channel includes moving one or more light sources (e.g., lasers) along the longitudinal axis of the flow channel. For instance, the light source may be moved upstream or downstream along the longitudinal axis of the flow channel irradiating the flow channel along a predetermined length of the flow channel. For example, methods may include moving the light source along the longitudinal axis of the flow channel for 1 mm or more, such as 2.5 mm or more, such as 5 mm or more, such as 10 mm or more, such as 15 mm or more, such as 25 mm or more and including 50 mm or more from the flow channel. The light source may be moved continuously or in discrete intervals. In some embodiments, the light source is moved continuously. In other embodiments, the light source is moved along the longitudinal axis of the flow channel in discrete intervals, such as for example in 0.1 mm or greater increments, such as 0.25 mm or greater increments and including 1 mm or greater increments.

In practicing methods according to aspects of the present disclosure, light emitted from the sample in the flow channel is measured at one or more wavelengths. In embodiments, emitted light is measured at one or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted from the sample in the flow channel at 400 or more different wavelengths.

In some embodiments, measuring light emitted from the sample in the flow channel includes measuring emitted light over a range of wavelengths (e.g., 200 nm-800 nm). For example, methods may include measuring light emitted from the sample in the flow channel over one or more of the wavelength ranges of: 200 nm-800 nm; 400 nm-500 nm; 500 nm-600 nm; 600 nm-700 nm; 700 nm-800 nm; 550 nm-600 nm; 600 nm-650 nm; 650 nm-700 nm and any portion or combinations thereof. In one instance, methods include measuring light emitted from the sample in the flow channel over the wavelengths ranging from 200 nm-800 nm. In another instance, methods include measuring light emitted from the sample in the flow channel over the wavelengths ranging from 500 nm-600 nm and 650 nm-750 nm. In certain instances, methods include measuring light emitted from the sample in the flow channel at 575 nm, 660 nm and 675 nm or a combination thereof.

Measuring light emitted from the sample in the flow channel over a range of wavelengths, in certain instances, includes collecting the spectra of the emitted light over the range of wavelengths. For example, methods may include collecting the spectra of light emitted from the sample in the flow channel over one or more of the wavelength ranges of: 200 nm-800 nm; 400 nm-500 nm; 500 nm-600 nm; 600 nm-700 nm; 700 nm-800 nm; 550 nm-600 nm; 600 nm-650 nm; 650 nm-700 nm and any portion or combinations thereof. In one instance, methods include collecting the spectra of emitted light from the sample in the flow channel over the wavelengths ranging from 400 nm-800 nm. In another instance, methods include collecting the spectra of emitted light from the sample in the flow channel over the wavelengths ranging from 500 nm-700 nm.

In certain embodiments, light emitted from the sample in the flow channel is detected at one or more specific wavelengths. For example, methods may include detecting light emitted from the sample in the flow channel at 2 or more specific wavelengths, such as at 3 or more specific wavelengths, such as at 4 or more specific wavelengths, such as at 5 or more specific wavelengths, such as at 10 or more specific wavelengths and including detecting light emitted from the sample in the flow channel at 25 or more specific wavelengths. In certain embodiments, the emitted light is detected at 575 nm. In other embodiments, the emitted light is detected at 660 nm. In yet other embodiments, the emitted light is detected at 675 nm.

Depending on the specific assay protocol, light emitted from the sample in the flow channel may be measured continuously or in discrete intervals. For example, in some embodiments, measuring emitted light is continuous throughout the entire time the sample is being assayed. Where measuring the emitted light includes measuring two or more wavelengths or wavelength ranges, the wavelengths or wavelength ranges may be all measured simultaneously, or each wavelength or wavelength range may be measured sequentially.

In other embodiments, emitted light is measured in discrete intervals, such as measuring light emitted from the sample in the flow channel every 0.001 microseconds, every 0.01 microseconds, every 0.1 microseconds, every 1 microsecond, every 10 microseconds, every 100 microseconds and including every 1000 microseconds. The light emitted from the sample from the flow channel may be measured one or more times during the subject methods, such 2 or more times, such as 3 or more times, such as 5 or more times and including 10 or more times.

Emitted light from the sample in the flow channel may be measured by any convenient light detecting protocol, including but not limited to optical sensors or photodetectors, such as active-pixel sensors (APSs), avalanche photodiode, image sensors, charge-coupled devices (CODs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the emitted light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, light is measured with a charge-coupled device (CCD). Where the emitted light is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

In some embodiments, methods include optically adjusting the emitted light from the flow channel. For example, the emitted light may be passed through one or more lenses, mirrors, pinholes, slits, gratings, light refractors, and any combinations thereof. In some instances, the emitted light is passed through one or more focusing lenses, such as to reduce the profile of the light propagated onto the active surface of the detector. In other instances, the emitted light is passed through one or more de-magnifying lenses, such as to increase the profile of the light propagated onto the active surface of the detector. In yet other instances, methods include collimating the light. For example, emitted light may be collimated by passing the light through one or more collimating lenses or collimating mirrors or a combination thereof.

In certain embodiments, methods include passing the emitted light collected from flow channel through fiber optics. Suitable fiber optics protocols for propagating light from the flow channel to the active surface of a detector include, but is not limited to, fiber optics protocols such as those described in U.S. Pat. No. 6,809,804, the disclosure of which is herein incorporated by reference.

In certain embodiments, methods including passing the emitted light through one or more wavelength separators. Wavelength separation, according to certain embodiments, may include selectively passing or blocking specific wavelengths or wavelength ranges of the polychromatic light. To separate wavelengths of light, the light may be passed through any convenient wavelength separating protocol, including but not limited to colored glass, bandpass filters, interference filters, dichroic mirrors, diffraction gratings, monochromators and combinations thereof, among other wavelength separating protocols.

In other embodiments, methods include separating the wavelengths of light by passing the emitted light from the flow channel through one or more optical filters, such as one or more bandpass filters. For example, optical filters of interest may include bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm.

In certain embodiments, the subject fluorescence assay may include methods for imaging samples in capillary channels such as those described in U.S. Pat. Nos. 8,248,597; 7,927,561 and 7,738,094 as well as those described in co-pending U.S. patent application Ser. No. 13/590,114 filed Aug. 20, 2012, 61/903,804 filed on Nov. 13, 2013 and 61/949,833 filed on Mar. 7, 2014, the disclosures of which are herein incorporated by reference.

In certain embodiments, methods include capturing an image of the flow channel. Capturing one or more images of the flow channel may include illuminating the flow channel with one or more light sources (as described above) and capturing the image with a charge-coupled device (CCD), semiconductor charge-coupled device (CCD), active pixel sensor (APS), complementary metal-oxide semiconductor (CMOS) image sensor or N-type metal-oxide semiconductor (NMOS) image sensor. Images of the flow channel may be captured continuously or in discrete intervals. In some instances, methods include capturing images continuously. In other instances, methods include capturing images in discrete intervals, such as capturing an image of the flow stream every 0.001 millsecond, every 0.01 millsecond, every 0.1 millsecond, every 1 millsecond, every 10 millseconds, every 100 millseconds and including every 1000 millseconds, or some other interval. Where images of the flow channel are captured with a CCD camera detector, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

All or part of the flow channel may be captured in each image, such as 5% or more of the flow channel, such as 10% or more, such as 25% or more, such as 50% or more, such as 75% or more, such as 90% or more, such as 95% or more and including 99% or more of the flow channel may be captured in each image. In certain embodiments, the entire flow channel is captured in each image. One or more images may be captured, as desired, such as 2 or more images, such, as 3 or more images, such as 5 or more images, such as 10 or more images, such as 25 or more images and including 100 or more images. Where more than one image is captured of the flow channel, the plurality of images may be automatically stitched together or averaged by a processor having digital image processing algorithm.

Images of the flow channel may be captured at any suitable distance from the flow channel so long as a usable image of the flow channel is captured. For example, images of the flow channel may captured at 0.01 mm or more from the flow stream, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more from the flow cytometer flow stream. Images of the flow channel may also be captured at any angle relative to the flow channel. For example, images of the flow channel may captured at an angle with respect to the longitudinal axis of the flow channel which ranges from 10° to 90°, such as from 15° to 85°, such as from 20° to 80°, such as from 25° to 75° and including from 30° to 60°. In certain embodiments, images of the flow channel are captured at a 90° angle with respect to the longitudinal axis of the flow channel.

In some embodiments, capturing images of the flow stream include moving one or more imaging sensors alongside the path of the flow stream. For instance, the imaging sensor may be moved upstream or downstream alongside the flow stream capturing images in a plurality of detection fields. For example, methods may include capturing images of the flow stream in two or more different detection fields, such as 3 or more detection fields, such as 4 or more detection fields and including 5 or more detections fields. The imaging sensor may be moved continuously or in discrete intervals. In some embodiments, the imaging sensor is moved continuously. In other embodiments, the imaging sensor may be moved along the flow stream path in discrete intervals, such as for example in 1 mm or greater increments, such as 2 mm or greater increments and including 5 mm or greater increments.

In certain embodiments, methods include reducing background signal from captured images of the flow channel. In these embodiments, methods include capturing an image of the flow channel with unbound optically-labeled analyte-specific binding members (i.e., assay reagent not mixed with the sample) and reducing (e.g., subtracting) the background signal from the captured images of the sample in the flow channel. In some instances, methods include capturing an image of the sample in the flow channel, determining the background signal from unbound optically-labeled analyte-specific binding members and reducing the background from the captured image of the sample in the flow channel. In embodiments of the present disclosure, the background signal may be determined one or more times, such as 2 or more times, such as 3 or more times, such as 5 or more times and including 10 or more times. Where desired, the background signal may be averaged to provide an average background signal. In certain embodiments, determining the background signal includes capturing one or more images of the flow channel in the absence of sample.

Depending on the assay reagents, unbound reagent in the flow channel is substantially constant. In other words, the distribution of unbound reagent present in the flow channel is homogeneous and the variation in amount of unbound reagent in different regions of the flow channel varies by 10% or less, such as by 5% or less, such as by 4% or less, such as by 3% or less, such as by 2% or less, such as by 1% or less, such as by 0.5% or less and including by 0.1% or less. Accordingly, the background signal varies along the longitudinal axis of the flow channel by 10% or less, such as by 5% or less, such as by 4% or less, such as by 3% or less, such as by 2% or less, such as by 1% or less, such as by 0.5% or less and including by 0.1% or less. In certain embodiments, methods include reducing the background signal from the captured image of the sample in the flow channel where the background signal varies by 10% or less, such as by 5% or less, such as by 4% or less, such as by 3% or less, such as by 2% or less, such as by 1% or less, such as by 0.5% or less and including by 0.1% or less along the longitudinal axis of the flow channel.

As illustrated in FIGS. 1 and 2A-B, microfluidic devices of interest may be used to detect serological concentrations of human antibodies in finger-stick volumes (5-50 μL) of whole blood in a no-wash format. In some certain embodiments, methods include applying a liquid sample to the sample application site and directing the sample flow via capillary force to the porous element. As the sample enters the porous element a reagent preparation dissolves in the sample at a substantially continuous rate. The assay mixture may comprise an optically active reagent for the specific labeling of component of the sample and a set of buffer components that provide for the continuous dissolution of the reagent in the sample. In some embodiments the buffer components may comprise bovine serum albumin (BSA), trehalose (such as $D^+$ trehalose), polyvinylpyrrolidone (PVP) or any combination thereof. The optically active reagent may be any detectable label such as a fluorescently labeled antibody conjugate. The buffer and sample may be mixed in the porous element via passive mixing though a network of tortuous paths in the porous element resulting in reagent that is bound to components of the sample and unbound reagent. The sample labeled with a detectable label may then be interrogated as discussed above, such as optically or magnetically along the capillary channel of the microfluidic device. In some embodiments the sample may be interrogated by obtaining a signal or image of the sample through a transmissive wall. Signal processing may include subtracting a background signal from unbound reagent. The amount of unbound reagent along the transmissive may be substantially constant. In some embodiments the amount of unbound reagent varies less than 50%, 40%, 30%, 20%, or 10%, along the transmissive wall, beneficially providing for improved detection of reagent bound to components of the sample. Detection may comprise subtraction of background optical signals and observing the number, optical properties, morphological or configuration of the signals above background.

Systems for Assaying a Sample for an Analyte

Aspects of the present disclosure further include systems for practicing the subject methods. In embodiments, systems which include one or more of the subject microfluidic devices and an optical interrogation system having a light source, and a detector for detecting one or more wavelengths of light emitted by the sample in the flow channel are provided. In certain embodiments, systems further include one or more of the subject microfluidic devices integrated directly into the optical interrogation system.

As summarized above, aspects of the present disclosure include assaying a sample for one or more analytes. Systems include one or more light sources for interrogating a flow channel containing a sample of interest mixed with an assay reagent. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 800 nm. Any convenient broadband light source protocol may be employed, such as a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, the light source is a narrow band light source emitting a particular wavelength or a narrow range of wavelengths. In some instances, the narrow band light sources emit light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Any convenient narrow band light source protocol may be employed, such as a narrow wavelength LED, laser diode or a broadband light source coupled to one or more optical bandpass filters, diffraction gratings, monochromators or any combination thereof. In certain embodiments, the narrow band light source is a laser, such as a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser, a dye laser, such as a stilbene, coumarin or rhodamine laser. In yet other instances, methods include irradiating the sample in the flow channel with a metal-vapor laser, such as a helium-cadmium (HeCd)

laser, helium-mercury (HeHg) laser, helium-selenium (HeSe) laser, helium-silver (HeAg) laser, strontium laser, neon-copper (NeCu) laser, copper laser or gold laser or a solid-state laser, such as a ruby laser, an Nd:YAG laser, NdCrYAG laser, Er:YAG laser, Nd:YLF laser, Nd:$YVO_4$ laser, Nd:$YCa_4O(BO_3)_3$ laser, Nd:YCOB laser, titanium sapphire laser, thulim YAG laser, ytterbium YAG laser, ytterbium$_2O_3$ laser or cerium doped lasers as well as combinations thereof.

The subject systems may include one or more light sources, as desired, such as two or more light sources, such as three or more light sources, such as four or more light sources, such as five or more light sources and including ten or more light sources. In embodiments, light sources emit light having wavelengths ranging from 200 nm to 1000 nm, such as from 250 nm to 950 nm, such as from 300 nm to 900 nm, such as from 350 nm to 850 nm and including from 400 nm to 800 nm.

As summarized above, the subject systems are configured to receive a microfluidic device having a sample application site, a flow channel in fluid communication with the sample application site and a porous component having a porous matrix and an assay reagent positioned between the sample application site and the flow channel. In these embodiments, systems may also include a cartridge holder for receiving the microfluidic into the subject system For example, the cartridge holder may include a support for receiving the microfluidic device and one or more cartridge retainers for maintaining the microfluidic device in the cartridge holder. In some instances, the cartridge holder includes vibration dampers for reducing agitation of the microfluidic device positioned in the cartridge holder as well as one or more cartridge presence flags configured to indicate that a microfluidic device is present in the cartridge holder.

In some embodiments, systems include a cartridge shuttle coupled to the cartridge holder for moving the microfluidic device into and out of the interrogation system. In some embodiments, the cartridge shuttle is coupled to one or more translation or lateral movement protocols to move the microfluidic device. For example, the cartridge shuttle may be coupled to a mechanically actuated translation stage, mechanical leadscrew assembly, mechanical slide device, mechanical lateral motion device, mechanically operated geared translation device, a motor-actuated translation stage, leadscrew translation assembly, geared translation device, such as those employing a stepper motor, servo motor, brushless electric motor, brushed DC motor, micro-step drive motor, high resolution stepper motor, among other types of motors. Systems may also include a set of rails for positioning the cartridge shuttle to facilitate lateral movement of the cartridge holder.

As described above, light emitted by the sample in the flow channel is collected and detected using one or photodetectors. In certain embodiments, systems include one or more objective lenses for collecting light emitted from the flow channel. For example, the objective lens may be a magnifying lens with a nominal magnification ranging from 1.2 to 5, such as a nominal magnification of from 1.3 to 4.5, such as a nominal magnification of from 1.4 to 4, such as a nominal magnification of from 1.5 to 3.5, such as a nominal magnification or from 1.6 to 3, including passing the transmitted light through a magnifying lens having a nominal magnification of from 1.7 to 2.5. Depending on the configuration of the light source, sample chamber and detector, properties of the objective lens may vary. For example, the numerical aperture of the subject objective lens may also vary, ranging from 0.01 to 1.7, such as from 0.05 to 1.6, such as from 0.1 to 1.5, such as from 0.2 to 1.4, such as from 0.3 to 1.3, such as from 0.4 to 1.2, such as from 0.5 to 1.1 and including a numerical aperture ranging from 0.6 to 1.0. Likewise, the focal length of the objective lens varies, ranging from 10 mm to 20 mm, such as from 10.5 mm to 19 mm, such as from 11 mm to 18 mm and including from 12 mm to 15 mm.

In some embodiments, the objective lens is coupled to an autofocus module for focusing light emitted from the flow channel onto the detector for detection. For example, a suitable autofocus module for focusing light emitted from the flow channel may include, but is not limited, to those described in U.S. Pat. No. 6,441,894, filed on Oct. 29, 1999, the disclosure of which is herein incorporated by reference.

Systems of the present disclosure may also include one or more wavelength separators. The term "wavelength separator" is used in its conventional sense to refer to an optical component configured to separate polychromatic light into component wavelengths such that each wavelength may be suitably detected. Examples of suitable wavelength separators in the subject systems may include but are not limited to colored glass, bandpass filters, interference filters, dichroic mirrors, diffraction gratings, monochromators and combinations thereof, among other wavelength separating protocols. Depending on the light source and sample being assayed, systems may include one or more wavelength separators, such as two or more, such as three or more, such as four or more, such as five or more and including 10 or more wavelength separators. In one example, systems include two or more bandpass filters. In another example, systems include two or more bandpass filters and a diffraction grating. In yet another example, systems include a plurality of bandpass filters and a monochromator. In certain embodiments, systems include a plurality of bandpass filters and diffraction gratings configured into a filter wheel setup. Where systems include two or more wavelength separators, the wavelength separators may be utilized individually or in series to separate polychromatic light into component wavelengths. In some embodiments, wavelength separators are arranged in series. In other embodiments, wavelength separators are arranged individually.

In some embodiments, systems include one or more diffraction gratings. Diffraction gratings of interest may include, but are not limited to transmission, dispersive or reflective diffraction gratings. Suitable spacings of the diffraction grating may vary ranging from 0.01 μm to 10 μm, such as from 0.025 μm to 7.5 μm, such as from 0.5 μm to 5 μm, such as from 0.75 μm to 4 μm, such as from 1 μm to 3.5 μm and including from 1.5 μm to 3.5 μm.

In some embodiments, systems include one or more optical filters. In certain instances, systems include bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm.

Systems of the present disclosure also include one or more detectors. Examples of suitable detectors may include, but are not limited to optical sensor or photodetectors, such as active-pixel sensors (APSs), avalanche photodiode, image sensors, charge-coupled devices (CODs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, light emitted from the flow channel is measured with a charge-coupled device (CCD). Where the emitted light is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

In some embodiments, systems include one or more cameras or camera sensors for capturing an image of the flow channel. Cameras suitable for capturing an image of the flow include, but are not limited to charge-coupled devices (CCD), semiconductor charge-coupled devices (CCD), active pixel sensors (APS), complementary metal-oxide semiconductor (CMOS) image sensors or N-type metal-oxide semiconductor (NMOS) image sensors.

In embodiments of the present disclosure, detectors of interest are configured to measure light emitted from the flow channel at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring the light transmitted through the sample chamber at 400 or more different wavelengths.

In embodiments, the detector may be configured to measure light continuously or in discrete intervals. In some instances, detectors of interest are configured to measure light continuously. In other instances, detectors of interest are configured to take measurements in discrete intervals, such as measuring light every 0.001 millsecond, every 0.01 millsecond, every 0.1 millsecond, every 1 millsecond, every 10 millseconds, every 100 millseconds and including every 1000 millseconds, or some other interval.

In certain embodiments, light emitted by the sample in flow channel is measured with an imaging system such as those described in U.S. Pat. Nos. 8,248,597; 7,927,561; 7,738,094 and in co-pending U.S. patent application Ser. No. 13/590,114 filed Aug. 20, 2012, 61/903,804 filed on Nov. 13, 2013 and 61/949,833 filed on Mar. 7, 2014, the disclosures of which are herein incorporated by reference In certain instances, systems of interest include one or more of the subject microfluidic devices (as described above) integrated into the imaging system. Accordingly, in these embodiments, the subject systems are not configured to receive a microfluidic device described above, but instead are configured to receive the fluid sample directly, which is subsequently removed following assay of the sample. By "removed" is meant that no amount of the sample remains in contact with the subject systems, including any of the flow channel, sample application site, inlet, as well as porous matrix. In other words, when the sample is removed, all traces of the sample are cleared from the components of the system. In some embodiments, systems may further include one or more washing devices for cleaning the integrated microfluidic device. For example, the washing devices may include microconduits with or without spray nozzles for delivering wash buffer to clean the microfluidic device. In certain embodiments, these systems include a reservoir for storage of one or more wash buffers.

Kits

Aspects of the invention further include kits, where kits include one or more microfluidic devices as described herein. In some instances, the kits can include one or more assay components (e.g., labeled reagents, buffers, etc., such as described above). In some instances, the kits may further include a sample collection device, e.g., a lance or needle configured to prick skin to obtain a whole blood sample, a pipette, etc., as desired. The various assay components of the kits may be present in separate containers, or some or all of them may be pre-combined. For example, in some instances, one or more components of the kit, e.g., the microfluidic devices, are present in a sealed pouch, e.g., a sterile foil pouch or envelope.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The methods, devices, and kits of the present disclosure find use in a variety of different applications and can be used to determine whether an analyte is present in a multitude of different sample types from a multitude of possible sources. Depending on the application and the desired output of the methods described herein, an analyte may be detected in a qualitative manner ("present" vs "absent"; "yes, above a predetermined threshold" vs "no, not above a predetermined threshold"; etc.) or a quantitative manner, e.g., as an amount in a sample (such as concentration in sample). Many different types of analytes can be analytes of interest, including but not limited to: proteins (including both free proteins and proteins bound to surface of a structure, such as a cell), nucleic acids, viral particles, and the like. Further, samples can be from in vitro or in vivo sources, and samples can be diagnostic samples.

In practicing methods of the present disclosure, the samples can be obtained from in vitro sources (e.g., extract from a laboratory grown cell culture) or from in vivo sources (e.g., a mammalian subject, a human subject, a research animal, etc.). In some embodiments, the sample is obtained from an in vitro source. In vitro sources include, but are not limited to, prokaryotic (e.g., bacterial) cell cultures, eukaryotic (e.g., mammalian, fungal) cell cultures (e.g., cultures of established cell lines, cultures of known or purchased cell lines, cultures of immortalized cell lines, cultures of primary cells, cultures of laboratory yeast, etc.), tissue cultures, column chromatography eluants, cell lysates/extracts (e.g., protein-containing lysates/extracts, nucleic acid-containing lysates/extracts, etc.), viral packaging supernatants, and the like. In some embodiments, the sample is obtained from an in vivo source. In vivo sources include living multi-cellular organisms and can yield diagnostic samples.

In some embodiments, the analyte is a diagnostic analyte. A "diagnostic analyte" is an analyte from a sample that has been obtained from or derived from a living multi-cellular organism, e.g., mammal, in order to make a diagnosis. In other words, the sample has been obtained to determine the presence of one or more disease analytes in order to diagnose a disease or condition. Accordingly, the methods are diagnostic methods. As the methods are "diagnostic methods," they are methods that diagnose (i.e., determine the presence or absence of) a disease (e.g., sickness, diabetes, etc.) or condition (e.g., pregnancy) in a living organism, such as a mammal (e.g., a human). As such, certain embodiments of the present disclosure are methods that are employed to determine whether a living subject has a given disease or condition (e.g., diabetes). "Diagnostic methods" also include methods that determine the severity or state of a given disease or condition.

In certain embodiments, the methods are methods of determining whether an analyte is present in a diagnostic sample. As such, the methods are methods of evaluating a sample in which the analyte of interest may or may not be present. In some cases, it is unknown whether the analyte is present in the sample prior to performing the assay. In other instances, prior to performing the assay, it is unknown whether the analyte is present in the sample in an amount that is greater than (exceeds) a predetermined threshold amount. In such cases, the methods are methods of evaluating a sample in which the analyte of interest may or may not be present in an amount that is greater than (exceeds) a predetermined threshold.

Diagnostic samples include those obtained from in vivo sources (e.g., a mammalian subject, a human subject, and the like.) and can include samples obtained from tissues or cells of a subject (e.g., biopsies, tissue samples, whole blood, fractionated blood, hair, skin, and the like). In some cases, cells, fluids, or tissues derived from a subject are cultured, stored, or manipulated prior to evaluation and such a sample can be considered a diagnostic sample if the results are used to determine the presence, absence, state, or severity of a disease (e.g., sickness, diabetes, etc.) or condition (e.g., pregnancy) in a living organism.

In some instances, a diagnostic sample is a tissue sample (e.g., whole blood, fractionated blood, plasma, serum, saliva, and the like) or is obtained from a tissue sample (e.g., whole blood, fractionated blood, plasma, serum, saliva, skin, hair, and the like). An example of a diagnostic sample includes, but is not limited to cell and tissue cultures derived from a subject (and derivatives thereof, such as supernatants, lysates, and the like); tissue samples and body fluids; non-cellular samples (e.g., column eluants; acellular biomolecules such as proteins, lipids, carbohydrates, nucleic acids; synthesis reaction mixtures; nucleic acid amplification reaction mixtures; in vitro biochemical or enzymatic reactions or assay solutions; or products of other in vitro and in vivo reactions, etc.); etc.

The subject methods can be employed with samples from a variety of different types of subjects. In some embodiments, a sample is from a subject within the class mammalia, including e.g., the orders carnivore (e.g., dogs and cats), rodentia (e.g., mice, guinea pigs, and rats), lagomorpha (e.g., rabbits) and primates (e.g., humans, chimpanzees, and monkeys), and the like. In certain embodiments, the animals or hosts, i.e., subjects are humans.

Example 1

The following example is offered by way of illustration and not by way of limitation. The example is provided for illustrative purposes only, and is not intended to limit the scope of the present disclosure in any way. Efforts have been made to ensure accuracy with respect to numbers used (e.g., amounts, temperatures, etc.), but some experimental error and deviation should, of course, be allowed for.

Figure 3:
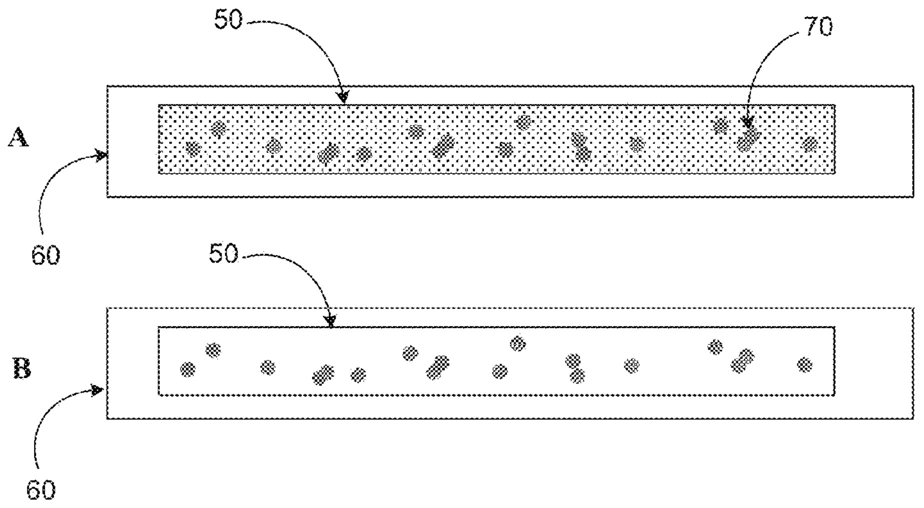
FIG. 3 panel A depicts an illustration of detecting components of a sample in the microfluidic device according to certain embodiments.

A finger-stick amount (5-50 μL) of whole blood is loaded into a sample application site of a capillary device of this invention (shown in FIGS. 2A and B) where it is drawn into the porous element via capillary force. The porous element is a porous frit and associated assay mixture. The reaction composition is a preserved buffer comprised of BSA, MES, $D^+$ trehalose, EDTA, PVP and a reagent mixture. The BSA:Trehalose:PVP ratio in a dry weight is 21:90:1. The reagent mixture is comprised of a set of antibody-dye conjugates, specific for antigens CD14, CD4, CD45RA, and CD3 in the blood sample. Once loaded, a cap is placed over the sample application site, sealing the sample application site and a vent outlet of the capillary channel. Capillary flow of the blood proceeds though the porous element and along the channel, unimpeded by the cap sealing the capillary from the outside environment. Flow may terminate at a hydrophobic junction. The anti-CD14, CD4, CD45RA, and CD3 antibodies present in the porous element dissolve into the blood sample at a substantially constant rate as the sample flows through the porous element and along the capillary channel for about 2 minutes from the time the sample was applied. The blood sample flows though the porous element substantially unimpeded and unfiltered. Specific components in the blood sample will bind to the dye-antibody conjugates, enabling the detection and quantification of analytes in the sample. Detection is carried out using an LED to illuminate the cartridge where the region of transmissive wall is located. The optical signal is measured by imaging through the optically transmissive wall of the capillary channel using a low power microscope with a CCD-camera detector and an appropriate filter. A schematic diagram of the image is shown in FIG. 3A through the transmissive wall 50 of the capillary channel 60. A schematic diagram of the image analysis results (FIG. 3B) shows that, after processing, the signal distribution of the dye-antibody conjugates bound to the analyte in cells is measurably higher than free conjugate in the sample stream. Image processing enables the reduction of background signal 70 in order to form a clearer image of cells labeled with the dye-antibody conjugates and determine the number of cells that tests positive for CD14, CD4, CD45RA, CD3 antibodies.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A microfluidic device comprising:

a sample application site;

a flow channel in fluid communication with the sample application site; and a porous component positioned between the sample application site and flow channel, wherein the porous component comprises:

a porous matrix comprising pores; and unbound dry assay reagent positioned within the pores of the porous matrix, wherein the porous matrix has a length sufficient for the unbound dry assay reagent and a sample to substantially mix, and wherein the porous matrix is configured to uniformly mix the assay reagent into a sample mixture flowing therethrough upon exit from the porous component and into the flow channel.

2. The microfluidic device according to claim 1, wherein the porous matrix is configured to be non-filtering with respect to the sample for which the device is configured to assay.

3. The microfluidic device according to claim 1, wherein the porous matrix comprises pores having diameters between 1 μm and 200 μm.

4. The microfluidic device according to claim 1, wherein the porous matrix comprises a pore volume between 1 μL and 25 μL.

5. The microfluidic device according to claim 1, wherein the porous matrix is a frit.

6. The microfluidic device according to claim 1, wherein the porous component further comprises a buffer.

7. The microfluidic device according to claim 6, wherein the buffer comprises bovine serum albumin (BSA), trehalose, polyvinylpyrrolidone (PVP) or 2-(N-morpholino) ethanesulfonic acid or a combination thereof.

8. The microfluidic device according to claim 7, wherein the buffer comprises BSA, trehalose and PVP.

9. The microfluidic device according to claim 1, wherein the assay reagent comprises an analyte-specific binding member.

10. The microfluidic device according to claim 9, wherein the analyte-specific binding member comprises an antibody or analyte binding fragment thereof.

11. The microfluidic device according to claim 9, wherein the analyte specific binding member is coupled to a detectable label.

12. The microfluidic device according to claim 11, wherein the detectable label comprises a fluorescent dye.

13. The microfluidic device according to claim 1, wherein the assay reagent comprises a chelating agent.

14. The microfluidic device according to claim 1, wherein the flow channel comprises an optically transmissive wall.

15. The microfluidic device according to claim 14, wherein the walls of the flow channel are optically transmissive to one or more of ultraviolet light, visible light and near-infrared light.

16. The microfluidic device according to claim 1, where the sample application site is configured to receive a sample having a volume ranging from 5 μL to 2000 μL.

17. The microfluidic device according to claim 1, wherein the device is configured to be hand held.

18. The microfluidic device according to claim 1, wherein the porous matrix comprises a porous organic polymer.

19. A kit comprising:

a microfluidic device comprising:

a sample application site;

a flow channel in fluid communication with the sample application site; and a porous component positioned between the sample application site and flow channel, wherein the porous component comprises a porous matrix comprising pores and unbound dry assay reagent positioned within the pores of the porous matrix, wherein the porous matrix has a length sufficient for the unbound dry assay reagent and a sample to substantially mix, and wherein the porous matrix is configured to uniformly mix the assay reagent into a sample mixture flowing therethrough upon exit from the porous component and into the flow channel; and a container housing the device.

* * * * *